(12) United States Patent  
Sato et al.

(10) Patent No.: US 6,329,116 B1  
(45) Date of Patent: *Dec. 11, 2001

(54) PYRROLO[1,2-A]PYRIMIDINE COMPOUND AND HEAT-SENSITIVE RECORDING MATERIAL USING THE SAME

(75) Inventors: Hiroshi Sato; Tatsuo Kawabuchi; Mitsuyuki Tsurumi; Tetsunori Matsushita; Hisato Nagase; Kimiatsu Nomura; Yoshihiro Jimbo; Kazunori Nigorikawa, all of Shizuoka-ken (JP)

(73) Assignee: Fuji Photo Film Co., Ltd., Kanagawa (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/441,957

(22) Filed: Nov. 17, 1999

(30) Foreign Application Priority Data

Nov. 20, 1998 (JP) .................................................. 10-331706  
Feb. 12, 1999 (JP) .................................................. 11-034018

(51) Int. Cl.[7] .............................. G03C 1/72; G03C 5/18; G03F 7/021; C07D 239/70
(52) U.S. Cl. .......................... 430/138; 430/157; 430/182; 430/186; 544/282; 544/284; 544/251; 544/293
(58) Field of Search .................... 430/138, 157, 430/186, 182; 544/284, 251, 282, 293

(56) References Cited

U.S. PATENT DOCUMENTS 5,925,489 * 7/1999 Kawabuchi et al. ................. 430/138  
6,060,206 * 5/2000 Hanaki et al. ....................... 430/138  
6,228,553 * 5/2001 Matsushita et al. ................. 430/179

FOREIGN PATENT DOCUMENTS 6-130600  5/1994  (JP) ................................. G03C/7/38

* cited by examiner

Primary Examiner—John S. Chu  
(74) Attorney, Agent, or Firm—Sughrue, Mion, Zinn, Macpeak & Seas, PLLC

(57) ABSTRACT

An object of the present invention is to provide a pyrrolo [1,2-a]pyrimidine compound that is useful as a coupler providing excellent hue of a cyan system and sufficient density of formed color. The pyrrolo[1,2-a]pyrimidine compound of the present invention for achieving the object is represented by one of following general formulae (1), (2) and (3).

General formula (1)

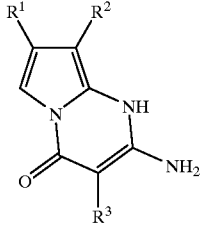

General formula (2)

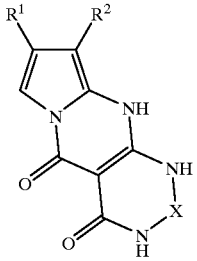

General formula (3)

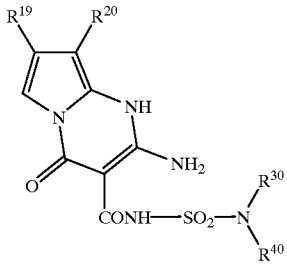

13 Claims, No Drawings

PYRROLO[1,2-A]PYRIMIDINE COMPOUND AND HEAT-SENSITIVE RECORDING MATERIAL USING THE SAME

BACKGROUND OF THE INVENTION

1. Field of the Invention

The present invention relates to a pyrrolo[1,2-a] pyrimidine compound that is useful as a coupler of a photographic material, a heat-sensitive recording material and the like, and to a heat-sensitive recording material that contains as color forming components the pyrrolo[1,2-a] pyrimidine compound serving as a coupler and a diazonium salt compound.

2. Description of the Related Art

With the recent advancement in performance of heat-sensitive recording materials, it has been strongly required to develop a heat-sensitive recording material that has cyan-color forming property and shows excellent hue, density of the formed color, and the like, in which shelf life, storability of images, image fixing property and the like are improved.

Diazonium salt compounds are compounds that have very high chemical activity and react with compounds called couplers (e.g., phenol derivatives, compounds having an active methylene group) to form an azo dye easily. Diazonium salt compounds are also light-sensitive and lose their activity when decomposed due to irradiation of light. Therefore, diazonium salt compounds have been used as light recording materials such as those used for diazo copies (see, "Shashin Kogaku no Kiso, Higin-en Shashin Hen (Fundamentals of Photographic Engineering, Edition of Non-Silver Salt Photography)" edited by Nippon Shashin Gakkai (Japan Photographic Association), Corona Co., Ltd. (1982), pp. 89 through 117, and pp. 182 through 201).

Further, by utilizing the property of diazonium salt compounds that they lose their activity due to decomposition by light, diazonium salt compounds have recently been used in recording materials that require fixing of images. As a representative example, there has been proposed a heat-sensitive recording material of a light fixing type in which a diazonium salt compound and a coupler are heated in accordance with image signals and react to form images, and thereafter, the images are fixed by irradiation of light (Hirotsugu Sato et al., "Gazo Denshi Gakkai Shi (Journal of the Image Electronics Society)", Vol. 11, No. 4 (1982), pp. 290–296, etc.).

However, the above-described recording materials using as a color forming element a diazonium salt compound have a drawback in that the activity of the diazonium salt compound is extremely high, and even in dark places, the diazonium salt compound thermally decomposes gradually such that the reactivity thereof is lost, and therefore, its shelf life as a recording material is short.

As one means for improving the above drawback, a method is known in which a diazonium salt compound is encapsulated in microcapsules. It has become possible by the above method to isolate the diazonium salt compound from substances promoting decomposition such as water, bases and the like, and to greatly improve the shelf life as a recording material (Tomomasa Usami et al., "Denshi Shashin Gakkai Shi (Journal of the Electrophotographic Association)", Vol. 26, No. 2, (1987), pp. 115 through 125). When the microcapsule is a microcapsule having a wall that has a glass transition temperature and in which the glass transition temperature is somewhat higher than room temperature such as urea resin and urethane resin, the capsule is called a heat-responsive microcapsule and is useful as a heat-sensitive recording material since, at room temperature, capsule walls exhibit non-permeability with respect to substances and, at the glass transition temperature or higher, exhibits permeability with respect to substances. In other words, if a heat-sensitive recording layer, which comprises heat-responsive microcapsules containing a diazonium salt compound, a coupler and a base, is applied onto a substrate to form a recording material, the diazonium salt compound can be kept stable for a long period of time, a color-formed image can be easily formed by heating, and further, the image can be fixed by irradiation of light.

As described above, it has become possible to greatly improve the stability of a diazonium salt compound by encapsulating the compound in microcapsules.

On the other hand, it is known that when 2-hydroxy-3-naphtoic anilides are used as couplers, they are excellent as color forming materials for heat-sensitive recording, and if a coupling reaction is effected with a 4-substituted amino-2-alkoxybenzene diazonium salt compound, a blue dye can be formed (Japanese Patent Application Laid-Open (JP-A) No. 2-225082).

However, the diazonium salt compound has a drawback in that, when a diazonium salt compound having $\lambda_{max}$ at a longer wavelength side is used, storability before use (background coloring property during storage before copying) of the recording material deteriorates. Further, in the case of a diazonium salt compound having $\lambda_{max}$ at a shorter wavelength side, when the aforementioned 2-hydroxy-3-naphtoic anilides are used, there are drawbacks in that the fixing property of images when irradiated with light is hindered, the hue extends over a long wavelength even to cyan, and further, storability of color-formed images (light fastness) is not sufficient.

As described above, there has not been obtained until now a heat-sensitive recording material that not only has a cyan color forming property but also provides excellent hue and sufficient density of the formed color, which results in satisfactory shelf life, image storability and image fixing property.

SUMMARY OF THE INVENTION

An object of the present invention is to provide a pyrrolo [1,2-a]pyrimidine compound that is useful as a coupler providing excellent hue of a cyan system and sufficient density of formed color, and a novel heat-sensitive recording material of a cyan color forming type that contains the pyrrolo[1,2-a]pyrimidine compound serving as a coupler and a diazonium salt compound so as to have excellent shelf life, image light-resistance, image fixing property and the like in addition to excellent hue and density of the formed color.

The present inventors have studied couplers intensively, and have found that novel pyrrolo[1,2-a]pyrimidine compounds represented by the following general formulae (1), (2) and (3) are useful as couplers that provide excellent hue of the cyan system and sufficient density of the formed color. Further, the inventors have found that a heat-sensitive recording material using the above pyrrolo[1,2-a]pyrimidine compound and a diazonium salt compound that will be described below has improved shelf life, image light-resistance and image fixing property, and has an excellent cyan color forming property. Thus, the inventors have accomplished the present invention.

A pyrrolo[1,2-a]pyrimidine compound according to a first aspect of the present invention is represented by following general formula (1):

General formula (1)

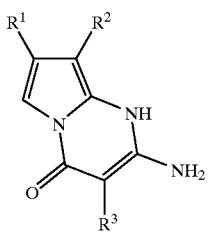

wherein, in the general formula (1), $R^1$ and $R^2$ each independently represents a hydrogen atom, halogen atom, aryl group, alkyl group, cyano group, acyl group, carbamoyl group, alkoxycarbonyl group, aryloxycarbonyl group, alkylsulfonyl group or arylsulfonyl group; and $R^3$ represents an electron attractive group whose Hammett's substituent constant $\sigma_p$ value is equal to or larger than 0.20.

A pyrrolo[1,2-a]pyrimidine compound according to a second aspect of the present invention is represented by following general formula (2):

General formula (2)

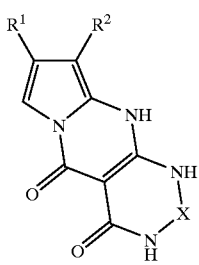

wherein, in the general formula (2), $R^1$ and $R^2$ each independently represents a hydrogen atom, halogen atom, aryl group, alkyl group, cyano group, acyl group, carbamoyl group, alkoxycarbonyl group, aryloxycarbonyl group, alkylsulfonyl group or arylsulfonyl group; and X represents CO or $SO_2$.

A pyrrolo[1,2-a]pyrimidine compound according to a third aspect of the present invention is represented by following general formula (3):

General formula (3)

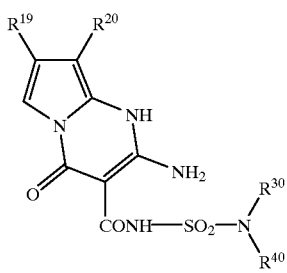

wherein, in the general formula (3), $R^{19}$ and $R^{20}$ each independently represents a hydrogen atom, halogen atom, aryl group, alkyl group, cyano group, acyl group, substituted carbamoyl group, alkoxycarbonyl group, aryloxycarbonyl group, acyloxy group, alkoxy group, aryloxy group, alkylthio group, arylthio group, substituted sulfamoyl group, alkylsulfonyl group, arylsulfonyl group, alkylphosphoryl group, arylphosphoryl group or substituted amino group; $R^{30}$ and $R^{40}$ each independently represents a hydrogen atom, alkyl group, aryl group, cycloalkyl group, piperidyl group, acyl group, $—C_nH_{2n}N(R^{50})(R^{60})$ or $—C_mH_{2m}XC_1H_{21}N(R^{70})(R^{80})$; $R^{50}$ through $R^{80}$ each independently represents a hydrogen atom, alkyl group or aryl group; X represents an oxygen atom, sulfur atom or $N(R^{90})—$; $R^{90}$ represents a hydrogen atom, alkyl group or aryl group; $R^{30}$ and $R^{40}$, or $R^{50}$ and $R^{60}$, or $R^{70}$ and $R^{80}$, or $R^{70}$ and $R^{90}$, or $R^{80}$ and $R^{90}$ may combine with each other to form a ring, and in the case of ring formation, they may contain a hetero atom; and n, m and l represent integers from 1 through 12.

A method of preparing a pyrrolo[1,2-a]pyrimidine compound of the present invention is a method of preparing the pyrrolo[1,2-a]pyrimidine compound of the third aspect of the present invention, wherein a pyrrolo[1,2-a]pyrimidine compound represented by following formula (A) is first reacted with chlorosulfonylisocyanate ($ClSO_2NCO$), and thereafter, reacted with $HN(R^{30})(R^{40})$:

(A)

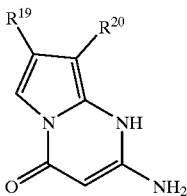

wherein, $R^{19}$ and $R^{20}$ in the formula (A) have the same meanings as those of $R^{19}$ and $R^{20}$ in the general formula (3) of the third aspect, respectively; and $R^{30}$ and $R^{40}$ in $HN(R^{30})(R^{40})$ have the same meanings as those of $R^{30}$ and R40 in the general formula (3) of the third aspect, respectively.

A heat-sensitive recording material of the present invention comprises a substrate, and on the substrate, a heat-sensitive recording layer contains a diazonium salt compound and a coupler that forms color by reacting with the diazonium salt compound during heating, wherein the coupler contains at least one type selected from the pyrrolo[1,2-a]pyrimidine compound represented by the general formula (1) of the first aspect, the pyrrolo[1,2-a]pyrimidine compound represented by the general formula (2) of the second aspect and the pyrrolo[1,2-a]pyrimidine compound represented by the general formula (3) of the third aspect of the present invention.

In a heat-sensitive recording material of the present invention, maximum absorption wavelength $\lambda_{max}$ of the diazonium salt compound is preferably 450 nm or less, and the diazonium salt compound is preferably at least one type of the compounds represented by one of following general formulae (4) through (6):

General formula (4)

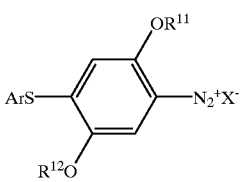

wherein, in the general formula (4), Ar represents a substituted or unsubstituted aryl group; $R^{11}$ and $R^{12}$ each independently represents a substituted or unsubstituted alkyl group, or a substituted or unsubstituted aryl group; $R^{11}$ and $R^{12}$ may be the same or different from each other; and $X^-$ represents an acid anion;

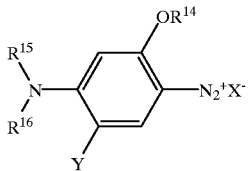

General formula (5)

wherein, in the general formula (5), $R^{14}$, $R^{15}$ and $R^{16}$ each independently represents a substituted or unsubstituted alkyl group, or a substituted or unsubstituted aryl group; $R^{14}$, $R^{15}$ and $R^{16}$ may be the same or different from each other; Y represents a hydrogen atom or a —$OR^{13}$ group; $R^{13}$ represents a substituted or unsubstituted alkyl group, or a substituted or unsubstituted aryl group; and $X^-$ represents an acid anion;

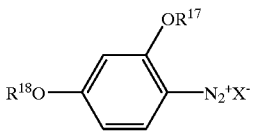

General formula (6)

wherein, in the general formula (6), $R^{17}$ and $R^{18}$ each independently represents a substituted or unsubstituted alkyl group, or a substituted or unsubstituted aryl group; and $X^-$ represents an acid anion.

Further, in a heat-sensitive recording material of the present invention, the diazonium salt compound is preferably encapsulated in microcapsules, and it is further preferable that capsule walls of the microcapsules comprise polyurethane and/or polyurea as components.

DETAILED DESCRIPTION OF THE PREFERRED EMBODIMENTS

A pyrrolo[1,2-a]pyrimidine compound of the present invention will be described in detail hereinafter. The pyrrolo [1,2-a]pyrimidine compound of the present invention has characteristics in which when it is coupled as a coupler with a diazonium salt compound, not only are excellent hue of a cyan system having little yellow light absorption and sufficient density of formed color obtained, but also light resistance is improved, and particularly excellent results regarding light resistance are obtained even under strict conditions, resulting in significantly reduced coloring of background portions.

The pyrrolo[1,2-a]pyrimidine compound of the present invention is a compound represented by one of the general formulae (1), (2) and (3).

In the formulae (1) and (2), $R^1$ and $R^2$ each independently represents a hydrogen atom, halogen atom, aryl group, alkyl group, cyano group, acyl group, carbamoyl group, alkoxycarbonyl group, aryloxycarbonyl group, alkylsulfonyl group or arylsulfonyl group. $R^3$ represents an electron attractive group whose value of Hammett's substituent constant $\sigma_p$ is equal to or larger than 0.20. X represents CO or $SO_2$.

Of the above values, as the substituents represented by $R^1$ and $R^2$, at least one of $R^1$ and $R^2$ is preferably an electron attractive group whose value of Hammett's substituent constant $\sigma_p$ is equal to or larger than 0.20, and it is further preferable that at least one of $R^1$ and $R^2$ is an electron attractive group whose value of $\sigma_p$ is equal to or larger than 0.35.

Examples of the electron attractive groups whose value of $\sigma_p$ is equal to or larger than 0.20 preferably include, but are not limited to, a cyano group (whose $\sigma_p$ value is 0.66), perfluoroalkyl group (for example, trifluoromethyl group whose $\sigma_p$ value is 0.54), acyl group (for example, acetyl group whose $\sigma_p$ value is 0.50, benzoyl group whose $\sigma_p$ value is 0.43), carbamoyl group (whose $\sigma_p$ value is 0.36), alkoxycarbonyl group (for example, ethoxycarbonyl group whose $\sigma_p$ value is 0.45) and the like.

Examples of the halogen atom include a fluorine atom, chlorine atom, bromine atom and the like, and a fluorine atom and chlorine atom are further preferable.

Examples of the electron attractive groups whose value of Hammett's substituent constant $\sigma_p$ is equal to or larger than 0.20 and that are represented by $R^3$ preferably include, but are not limited to, an aryl group, cyano group, acyl group, carbamoyl group, alkoxycarbonyl group, aryloxycarbonyl group, alkylsulfonyl group, arylsulfonyl group, alkylphosphoryl group, arylphosphoryl group, perfluoroalkyl group and the like.

Of the substituents represented by $R^1$ through $R^3$, the aryl group may be substituted further by an alkyl group, alkoxy group, aryloxy group, halogen atom, nitro group, cyano group, substituted carbamoyl group, substituted sulfamoyl group, substituted amino group, substituted oxycarbamoyl group, substituted oxysulfonyl group, alkylthio group, arylthio group, alkylsulfonyl group, arylsulfonyl group, aryl group, hydroxy group, acyl group, acyloxy group, substituted sulfonyloxy group, substituted aminocarbonyloxy group, substituted phosphoryloxy group or the like.

When $R^1$ and $R^2$ each independently represents an aryl group, an aryl group having 6 through 30 carbon atoms is preferable as the aryl group, and examples thereof include not only a phenyl group, 2-methylphenyl group, 2-chlorophenyl group, 2-methoxyphenyl group, 2-ethoxyphenyl group, 2-propoxyphenyl group, 2-isopropoxyphenyl group, 2-butoxyphenyl group, 2-(2-ethylhexyloxy)phenyl group, 2-octyloxyphenyl group, 2-undecyloxyphenyl group, 2-trifluoromethylphenyl group, 2-(2-ethylhexyloxy)-5-chlorophenyl group, 2-(2-ethylhexyloxy)-3,5-dichlorophenyl group, 3-(2,4-di-t-pentylphenoxyethoxy)phenyl group, 2-(dibutylaminocarbonylethoxy)phenyl group, 2,4-dichlorophenyl group, 2,5-dichlorophenyl group, 2,4,6-trimethylphenyl group, 3-chlorophenyl group, 3-nitrophenyl group, 3-cyanophenyl group, 3-trifluoromethylphenyl group, 3-methoxyphenyl group, 3-ethoxyphenyl group, 3-butoxyphenyl group, 3-(2-ethylhexyloxy)phenyl group, 3,4-dichlorophenyl group, 3,5-dichlorophenyl group, 3,4-dimethoxyphenyl group, 3,5-dibutoxyphenyl group, 3-octyloxyphenyl group, 3-(dibutylaminocarbonylmethoxy) phenyl group, 3-(di-2-ethylhexylaminocarbonylmethoxy) phenyl group, 3-dodecyloxyphenyl group, 4-chlorophenyl group, 4-cyanophenyl group, 4-nitrophenyl group, 4-trifluoromethylphenyl group, 4-methoxyphenyl group, 4-ethoxyphenyl group, 4-isopropoxyphenyl group, 4-butoxyphenyl group, 4-(2-ethylhexyloxy)phenyl group, 4-isopentyloxyphenyl group, 4-(octadecyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexyloxycarbonyl)phenyl group, 4-t-octylphenyl group, 4-fluorophenyl group, 3-acetylphenyl group, 2-acetylaminophenyl group, 2,4-di-t-pentylphenyl group, 4-(2-ethylhexyloxy)carbonylphenyl group, 4-methylthiophenyl group and 4-(4-chlorophenylthio) phenyl group, but also hydroxyphenyl group, phenylsulfonylphenyl group, phenylsulfonyloxyphenyl group, phenylcarbonyloxyphenyl group, dimethylaminocarbonyloxyphenyl group, butylcarbonyloxyphenyl group and the like.

When $R^3$ represents an aryl group, an aryl group having 6 through 30 carbon atoms is preferable as the aryl group, and examples thereof include a 3-nitrophenyl group, 4-nitrophenyl group, 4-cyanophenyl group, 4-trifluoromethylphenyl group, 4-methylsulfonylphenyl group, 4-ethylsulfonylfphenyl group, 4-octylsulfonylphenyl group, 4-phenylsulfonylphenyl group, pentafluorophenyl group, pentachlorophenyl group and the like.

Of the substituents represented by $R^1$ and $R^2$, the alkyl group may be linear or branched, and may have an unsaturated bond. Further, the above alkyl group may be substituted by an alkoxy group, aryloxy group, alkoxycarbonyl group, aryloxycarbonyl group, aryl group, hydroxy group, halogen atom or the like. Likewise, the aryl group described above may further be substituted by an alkyl group, alkoxy group, nitro group, cyano group, hydroxy group or halogen atom.

When $R^1$ and $R^2$ each independently represents an alkyl group, an alkyl group having 1 through 30 carbon atoms is preferable as the alkyl group, and examples thereof include a methyl group, trifluoromethyl group, ethyl group, butyl group, hexyl group, octyl group, 2-ethylhexyl group, decyl group, dodecyl group, octadecyl group, propyl group, isopropyl group, isobutyl group, sec-butyl group, t-butyl group, pentyl group, 1-ethylpentyl group, cyclopentyl group, cyclohexyl group, isopentyl group, heptyl group, nonyl group, undecyl group, propenyl group, heptadecenyl group, t-octyl group, ethoxycarbonylmethyl group, butoxycarbonylmethyl group, 2-ethylhexyloxycarbonylmethyl group, 1-(ethoxycarbonyl)ethyl group, 2',4'-diisopentylphenyloxymethyl group, 2',4'-di-t-butylphenyloxymethyl group, ethoxycarbonylethyl group, 2-ethylhexyloxycarbonylethyl group, butyldecyloxycarbonylethyl group, dibutylaminocarbonylmethyl group, dibenzylaminocarbonylethyl group, ethyloxycarbonylpropyl group, 2-ethylhexyloxycarbonylpropyl group, 2,4-di-t-amylphenyloxypropyl group, 1-(2',4'-di-t-amylphenyloxy) propyl group, 2,4-di-t-butylphenyloxypropyl group, acetylaminoethyl group, N,N-dihexylaminocarbonylethyl group, 2,4-di-t-amyloxyethyloxycarbonylpropyl group, isostearyloxycarbonylpropyl group, 1-(2,4-di-t-pentylphenyloxy) propyl group, 2,4-di-t-pentylphenyloxyethyloxycarbonylpropyl group, naphthyloxyethyloxycarbonylethyl group, N-methyl-N-phenylethyloxycarbonylethyl group, methanesulfonylaminopropyl group and the like.

Of the substituents represented by $R^1$ through $R^3$, an acyl group having 2 through 20 carbon atoms is preferable as the acyl group, and examples thereof include an acetyl group, propanoyl group, butanoyl group, hexanoyl group, octanoyl group, 2-ethylhexanoyl group, decanoyl group, dodecanoyl group, octadecanoyl group, 2-cyanopropanoyl group, 1,1-dimethylpropanoyl group, benzoyl group, 2-(2,4-di-t-pentylphenyloxy) butanoyl group, phenoxyacetyl group and the like.

Of the substituents represented by $R^1$ through $R^3$, the carbamoyl group may be a substituted or unsubstituted carbamoyl group, and examples thereof include a carbamoyl group, N-alkylcarbamoyl group, N-arylcarbamoyl group, N-acylcarbamoyl group, N-alkoxycarbonylcarbamoyl group, N-aryloxycarbonylcarbamoyl group, N-alkylsulfonylcarbamoyl group, N-arylsulfonylcarbamoyl group, N,N-dialkylcarbamoyl group, N,N-diarylcarbamoyl group, N-alkyl-N-arylcarbamoyl group and the like.

As the substituted carbamoyl group, a substituted carbamoyl group having 1 through 30 carbon atoms is preferable, and examples thereof include an N-methylcarbamoyl group, N-ethylcarbamoyl group, N-propylcarbamoyl group, N-butylcarbamoyl group, N-hexylcarbamoyl group, N-cyclohexylcarbamoyl group, N-octylcarbamoyl group, N-2-ethylhexylcarbamoyl group, N-decylcarbamoyl group, N-octadecylcarbamoyl group, N-phenylcarbamoyl group, N-2-methylphenylcarbamoyl group, N-2-chlorophenylcarbamoyl group, N-2-methoxyphenylcarbamoyl group, N-2-isopropoxyphenylcarbamoyl group, N-2-(2-ethylhexyloxy) phenylcarbamoyl group, N-3-chlorophenylcarbamoyl group, N-3-nitrophenylcarbamoyl group, N-3-cyanophenylcarbamoyl group, N-4-methoxyphenylcarbamoyl group, N-4-(2-ethylhexyloxy) phenylcarbamoyl group, N-4-cyanophenylcarbamoyl group, N-acetylcarbamoyl group, N-benzoylcarbamoyl group, N-methoxycarbonylcarbamoyl group, N-ethoxycarbonylcarbamoyl group, N-butoxycarbonylcarbamoyl group, N-phenoxycarbonylcarbamoyl group, N-methylsulfonylcarbamoyl group, N-ethylsulfonylcarbamoyl group, N-isopropylsulfonylcarbamoyl group, N-butylsulfonylcarbamoyl group, N-octylsulfonylcarbamoyl group, N-phenylsulfonylcarbamoyl group, N-(4-methylphenyl) sulfonylcarbamoyl group, N-(4-chlorophenyl) sulfonylcarbamoyl group, N-(4-methoxyphenyl) sulfonylcarbamoyl group, N-[4-(2-ethylhexyloxy)phenyl] sulfonylcarbamoyl group, N,N-dimethylcarbamoyl group, N,N-dibutylcarbamoyl group, N,N-diphenylcarbamoyl group, N-methyl-N-phenylcarbamoyl group and the like.

Of the substituents represented by $R^1$ through $R^3$, an alkoxycarbonyl group having 2 through 20 carbon atoms is preferable as the alkoxycarbonyl group, and examples thereof include a methoxycarbonyl group, ethoxycarbonyl group, propoxycarbonyl group, butoxycarbonyl group, hexyloxycarbonyl group, 2-ethylhexyloxycarbonyl group, octyloxycarbonyl group, decyloxycarbonyl group, octadecyloxycarbonyl group, phenyloxyethyloxycarbonyl group, phenyloxypropyloxycarbonyl group, 2,4-di-t-amylphenyloxyethylcarbonyl group, 2,6-di-t-butyl-4-methylcyclohexyloxycarbonyl group, isostearyloxycarbonyl group and the like.

Of the substituents represented by $R^1$ through $R^3$, an aryloxycarbonyl group having 7 through 30 carbon atoms is preferable as the aryloxycarbonyl group, and examples thereof include a 2-methylphenyloxycarbonyl group, 2-chlorophenyloxycarbonyl group, 2,6-dimethylphenyloxycarbonyl group, 2,4,6-trimethylphenyloxycarbonyl group, 2-methoxyphenyloxycarbonyl group, 2-butoxyphenyloxycarbonyl group, 3-cyanophenyloxycarbonyl group, 3-nitrophenyloxycarbonyl group, 2,2-ethylhexylphenyloxycarbonyl group, 3-(2-ethylhexyloxy) phenyloxycarbonyl group, 4-fluorophenyloxycarbonyl group, 4-chlorophenyloxycarbonyl group, 4-cyanophenyloxycarbonyl group, 4-butoxyphenyloxycarbonyl group and the like.

Of the substituents represented by $R^1$ through $R^3$, an alkylsulfonyl group having 1 through 20 carbon atoms is preferable as the alkylsulfonyl group, and examples thereof include a methylsulfonyl group, ethylsulfonyl group, propylsulfonyl group, isopropylsulfonyl group, butylsulfonyl group, hexylsulfonyl group, cyclohexylsulfonyl group, octylsulfonyl group, 2-ethylhexylsulfonyl group, decanoylsulfonyl group, dodecanoylsulfonyl group, octadecanoylsulfonyl group, cyanomethylsulfonyl group and the like.

Of the substituents represented by $R^1$ through $R^3$, an arylsulfonyl group having 6 through 30 carbon atoms is preferable as the arylsulfonyl group, and examples thereof include a phenylsulfonyl group, 1-naphthylsulfonyl group, 2-naphthylsulfonyl group, 2-chlorophenlsulfony group, 2-methylphenylsulfonyl group, 2-methoxyplhenylsulfonyl group, 2-butoxyphelnylsulfonyl group, 3-chlorophenylsulfonyl group, 3-trifluoromethylplienylsulfonyl group, 3-cyanophenylsulfonyl group, 3-(2-ethylhexyloxy)phenylsulfonyl group, 3-nitrophenylsulfonyl group, 4-fluorophenylsulfonyl group, 4-chlorophenylsulfonyl group, 4-methylphenylsulfonyl group, 4-cyanophenylsulfonyl group, 4-butoxyphenylsulfonyl group, 4-(2-ethylhexyloxy)phenylsulfonyl group, 4-octadecylphenylsulfonyl group and the like.

Of the substituents represented by $R^3$, an alkylphosphoryl group having 2 through 40 carbon atoms is preferable as the alkylphosphoryl group, and examples thereof include a methylphosphoryl group, ethylphosphoryl group, propylphosphoryl group, isopropylphosphoryl group, butylphosphoryl group, isobutylphosphoryl group, sec-butylphosphoryl group, t-butylphosphoryl group, pentylphosphoryl group, isopentylphosphoryl group, hexylphosphoryl group, heptylphosphoryl group, octylphosphoryl group, 2-ethylhexylphosphoryl group, decylphosphoryl group, dodecylphosphoryl group, octadecylphosphoryl group, ethoxycarbonylmethylphosphoryl group, 2-ethylhexyloxycarbonylmethylphosphoryl group, aminocarbonylmethylphosphoryl group, N,N-dibutylaminocarbonylmethylphosphoryl group, N-methylaminocarbonylmethylphosphoryl group, N-ethylaminocarbonylmethylphosphoryl group, N-octylaminocarbonylmethylphosphoryl group, benzylphosphoryl group and the like.

Of the substituents represented by $R^3$, an arylphosphoryl group having 12 through 50 carbon atoms is preferable as the arylphosphoryl group, and examples thereof include a phenylphosphoryl group, 1-naphthylphosphoryl group, 2-naphthylphosploryl group, 2-chlorophenylphosphory group, 2-methylphenylphosphoryl group, 2-methoxyphenylphosphoryl group, 2-butoxy phenylphosphoryl group, 3-chlorophenlyphosphoryl group, 3-trefluoromethylphenylphosphoryl group, 3-cyanophenylphosphoryl group, 3-(2-ethylhexyloxy) phenylphosphoryl group, 3-nitrophenytphosphoryl group, 4-fluorophenylphosphoryl group, 4-cyanophenylphosphoryl group, 4-butoxyphenylphosphoryl group, 4-(2-ethylhexyloxy)phenylphosphoryl group, 4-octadecylphenylphosphoryl group and the like.

Of the substituent represented by $R^3$, a perfluoroalkyl group having 1 through 20 carbon atoms is preferable as the perfluoroalkyl group, and examples thereof include a trifluoromethyl group, pentafluoroethyl group, heptafluoropropyl group, nonafluorobutyl group and the like.

Of the above substituents, an alkyl group or aryl group is preferable as the substltuents represented by $R^1$, and an aryl group is further preferable.

A cyano group or alkoxycarbonyl group is preferable as the substituents represented by $R^2$, and an alkoxycarbonyl group is further preferable.

A carbamoyl group is preferable as the substituents represented by $R^3$, and an N-arylsulfonylcarbamoyl group is further preferable.

Specific examples of the pyrrolo[1,2-a]pyrimidine compound represented by the general formulae (1) and (2) are given below. However, the pyrrolo[1,2-a]pyrimidine of the present invention is not limited to the followng examples. It is to be noted that $R^1$ through $R^3$ and X in the following Tables 1 through 7 represent symbols in the general formulae (1) and (2).

TABLE 1

| No. | $R^1$ | $R^2$ | $R^3$ |
|---|---|---|---|
| 1 | phenyl | —CN | —COCH$_3$ |
| 2 | phenyl | —CN | —COC$_3$H$_7$(n) |

TABLE 1-continued
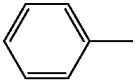
| No. | R¹ | R² | R³ |
|---|---|---|---|
| 3 | 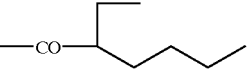 | —CN | 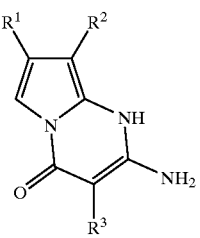 |
| 4 | 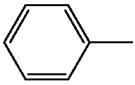 | —CN | 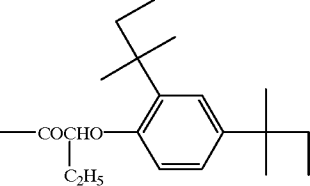 |
| 5 | 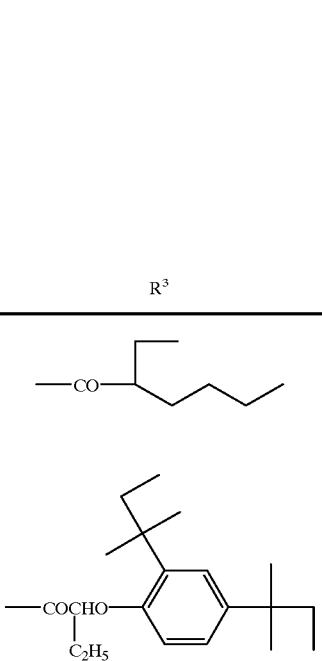 | —CN | 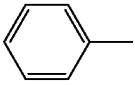 |
| 6 | 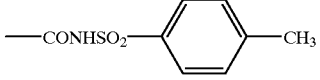 | 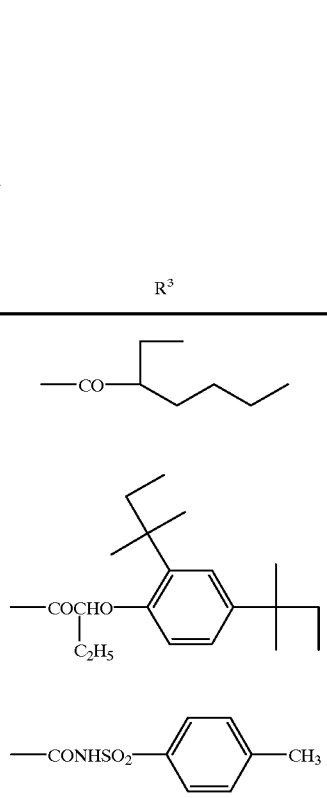 | —COCH₃ |
| 7 | 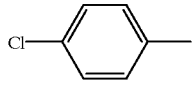 | 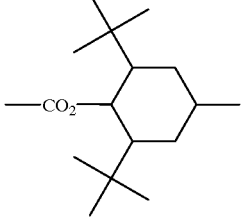 |  |
| 8 | 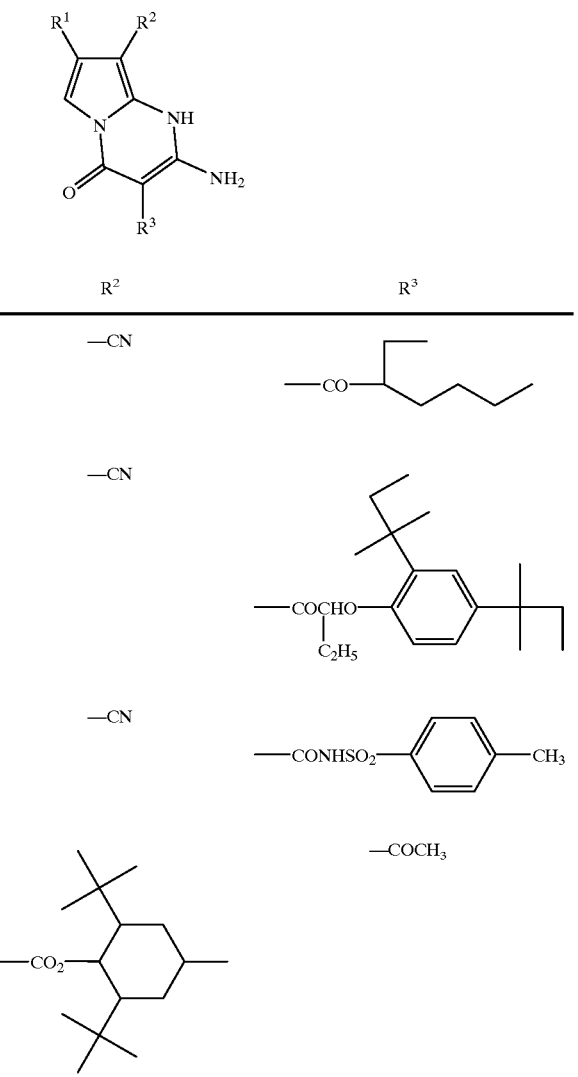 |  | 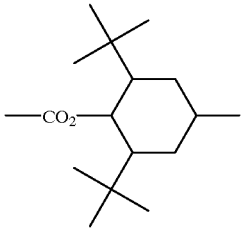 |

TABLE 2

| No. | R¹ | R² | R³ |
|---|---|---|---|
| 9 | 4-Cl-C₆H₄- | -CO₂-(2,6-di-tert-butyl-4-methylcyclohexyl) | -CONH-C₆H₄-4-Cl |
| 10 | 3,4-di-Cl-C₆H₃- | -CO₂-(2,6-di-tert-butyl-4-methylcyclohexyl) | -CONHSO₂-C₆H₄-4-Cl |
| 11 | 3,4-di-Cl-C₆H₃- | -CO₂-(2,6-di-tert-butyl-4-methylcyclohexyl) | -CONHSO₂-C₆H₅ |
| 12 | 4-Cl-C₆H₄- | -CO₂-(2,6-di-tert-butyl-4-methylcyclohexyl) | -CONHSO₂-C₆H₄-4-CH₃ |
| 13 | 4-F-C₆H₄- | -CO₂-(2,6-di-tert-butyl-4-methylcyclohexyl) | -CONHSO₂-C₆H₄-4-CH₃ |
| 14 | 4-CF₃-C₆H₄- | -CO₂-(2,6-di-tert-butyl-4-methylcyclohexyl) | -CONHSO₂-C₆H₄-4-CH₃ |

TABLE 2-continued

| No. | R¹ | R² | R³ |
|-----|----|----|----|
| 15 | 2-chlorophenyl | —CO$_2$—(2,6-di-tert-butyl-4-methylcyclohexyl) | —CONHSO$_2$—C$_6$H$_4$—CH$_3$ (para) |
| 16 | 3-chlorophenyl | —CO$_2$—(2,6-di-tert-butyl-4-methylcyclohexyl) | —CONHSO$_2$—C$_6$H$_4$—CH$_3$ (para) |
| 17 | 2,4-dichlorophenyl | —CO$_2$—(2,6-di-tert-butyl-4-methylcyclohexyl) | —CONHSO$_2$—C$_6$H$_4$—CH$_3$ (para) |
| 18 | 3,4-dichlorophenyl | —CO$_2$—(2,6-di-tert-butyl-4-methylcyclohexyl) | —CONHSO$_2$—C$_6$H$_4$—CH$_3$ (para) |

TABLE 3

| No. | R¹ | R² | R³ |
|-----|----|----|----|
| 19 | 3,4-dichlorophenyl | —CO$_2$CH$_3$ | —CONHSO$_2$—C$_6$H$_4$—CH$_3$ (para) |
| 20 | 3,4-dichlorophenyl | —CO$_2$C$_2$H$_5$ | —CONHSO$_2$—C$_6$H$_4$—CH$_3$ (para) |
| 21 | 4-chlorophenyl | —CO$_2$CH$_3$ | —CONHSO$_2$—C$_6$H$_4$—CH$_3$ (para) |

TABLE 3-continued

| No. | R¹ | R² | R³ |
|---|---|---|---|
| 22 | 4-Cl-C₆H₄— | —CO₂C₂H₅ | —CONHSO₂—C₆H₄—CH₃ (4-) |
| 23 | 4-Cl-C₆H₄— | —CO₂C₃H₇(n) | —CONHSO₂—C₆H₄—CH₃ (4-) |
| 24 | 4-Cl-C₆H₄— | —CO₂C₃H₇(i) | —CONHSO₂—C₆H₄—CH₃ (4-) |
| 25 | 4-Cl-C₆H₄— | —CO₂CH₂CH(C₂H₅)C₄H₉ | —CONHSO₂—C₆H₄—CH₃ (4-) |
| 26 | 3,4-Cl₂-C₆H₃— | —CO₂-(2,6-di-t-Bu-4-methylcyclohexyl) | —CONHCO₂C₂H₅ |
| 27 | (CH₃)₂CH— | —CO₂-(2,6-di-t-Bu-4-methylcyclohexyl) | —CONHSO₂—C₆H₄—CH₃ (4-) |
| 28 | —CF₃ | —CO₂-(2,6-di-t-Bu-4-methylcyclohexyl) | —CONHSO₂—C₆H₄—CH₃ (4-) |

TABLE 4

| No. | R¹ | R² | R³ |
|---|---|---|---|
| 29 | 4-Cl-C₆H₄— | —CONH₂ | —CONHSO₂—C₆H₄—CH₃ (4-) |
| 30 | 4-Cl-C₆H₄— | —CON(CH₃)₂ | —CONHSO₂—C₆H₄—CH₃ (4-) |

TABLE 4-continued

| No. | R¹ | R² | R³ |
|---|---|---|---|
| 31 | 4-Cl-C₆H₄- | —CONHCH₃ | —CONHSO₂-C₆H₄-4-CH₃ |
| 32 | 4-Cl-C₆H₄- | —SO₂-C₆H₅ | —CONHSO₂-C₆H₄-4-CH₃ |
| 33 | 4-Cl-C₆H₄- | —SO₂-(2-Cl-C₆H₄) | —CONHSO₂-C₆H₄-4-CH₃ |
| 34 | 4-Cl-C₆H₄- | —SO₂-C₆H₄-4-Cl | —CONHSO₂-C₆H₄-4-CH₃ |
| 35 | 4-Cl-C₆H₄- | —SO₂CH₃ | —CONHSO₂-C₆H₄-4-CH₃ |
| 36 | C₆H₅- | —CO₂-(2,6-di-t-Bu-4-Me-cyclohexyl) | 4-NO₂-C₆H₄- |
| 37 | C₆H₅- | —CO₂-(2,6-di-t-Bu-4-Me-cyclohexyl) | —CO₂C₂H₅ |
| 38 | C₆H₅- | —CO₂-(2,6-di-t-Bu-4-Me-cyclohexyl) | —CO₂C₈H₁₇(n) |

TABLE 5

| No. | R¹ | R² | R³ |
|-----|----|----|----|
| 39 | phenyl | 2,6-di-tert-butyl-4-methylcyclohexyl-CO₂– | –CO₂CH₂CH(C₂H₅)C₄H₉ |
| 40 | phenyl | 2,6-di-tert-butyl-4-methylcyclohexyl-CO₂– | –CO₂-phenyl |
| 41 | phenyl | 2,6-di-tert-butyl-4-methylcyclohexyl-CO₂– | –SO₂CH₃ |
| 42 | phenyl | 2,6-di-tert-butyl-4-methylcyclohexyl-CO₂– | –SO₂-phenyl |
| 43 | phenyl | 2,6-di-tert-butyl-4-methylcyclohexyl-CO₂– | –SO₂-C₆H₄-CH₃ |
| 44 | phenyl | 2,6-di-tert-butyl-4-methylcyclohexyl-CO₂– | –P(=O)(OC₂H₅)₂ |

TABLE 5-continued
| No. | R¹ | R² | R³ |
|---|---|---|---|
| 45 | phenyl- | 2,6-di-tert-butyl-4-methylcyclohexyl-CO₂- | $-\overset{O}{\underset{\|}{P}}(-O-\text{phenyl})_2$ |
| 46 | phenyl- | 2,6-di-tert-butyl-4-methylcyclohexyl-CO₂- | —CF₃ |
| 47 | phenyl- | 2,6-di-tert-butyl-4-methylcyclohexyl-CO₂- | —CN |
TABLE 6
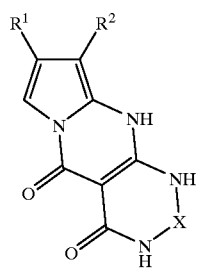
| No. | R¹ | R² | X |
|---|---|---|---|
| 48 | phenyl- | 2,6-di-tert-butyl-4-methylcyclohexyl-CO₂- | >SO₂ |

TABLE 6-continued
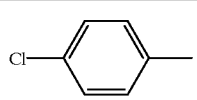
| No. | R¹ | R² | X |
|---|---|---|---|
| 49 | 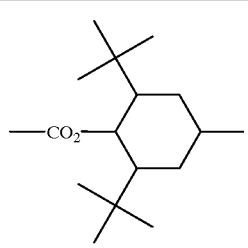 |  | 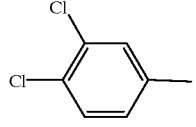 |
| 50 | 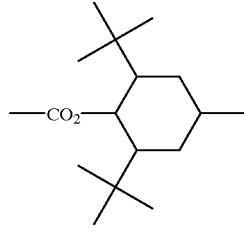 |  | 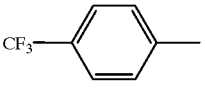 |
| 51 | 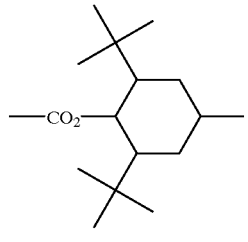 |  | 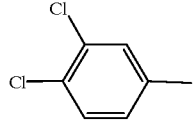 |
| 52 | 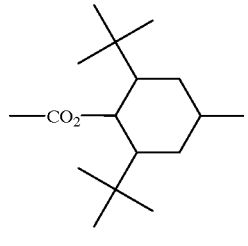 |  | 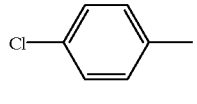 |
| 53 | 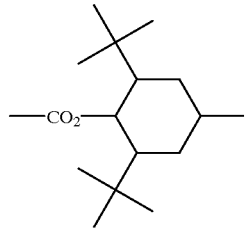 |  | |

TABLE 6-continued
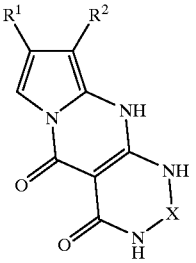
| No. | R¹ | R² | X |
|---|---|---|---|
| 54 | 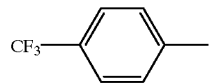 | 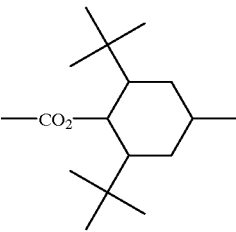 |  |
| 55 | 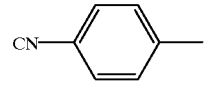 | 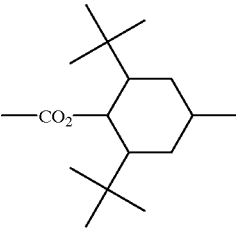 |  |
TABLE 7
| No. | R¹ | R² | X |
|---|---|---|---|
| 56 | 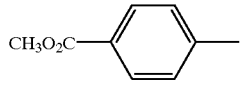 | 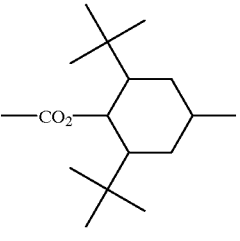 |  |
| 57 | 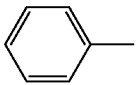 | 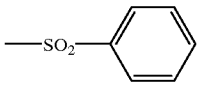 |  |
| 58 | 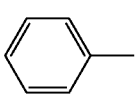 | —SO₂CH₃ |  |
| 59 |  | —CO₂C₂H₅ | 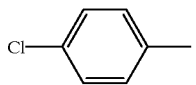 |

TABLE 7-continued

| No. | R¹ | R² | X |
|---|---|---|---|
| 60 | 3,4-dichlorophenyl | —CO$_2$C$_2$H$_5$ | >SO$_2$ |
| 61 | 4-chlorophenyl | —CO$_2$C$_2$H$_5$ | >CO |
| 62 | 3,4-dichlorophenyl | —CO$_2$C$_2$H$_5$ | >CO |
| 63 | 4-(CF$_3$)phenyl | —CO$_2$C$_2$H$_5$ | >CO |
| 64 | 4-(CF$_3$)phenyl | —CO$_2$C$_2$H$_5$ | >SO$_2$ |

Next, a method of preparing the pyrrolo[1,2-a]pyrimidine compounds represented by the general formulae (1) and (2), respectively, will be described.

The compound of the present invention represented by the general formula (1) can be obtained by reacting the pyrrolo [1,2-a]pyrimidine compound having an amino group (hereinafter, simply referred to as "amino structure A") with R³—X (X=halogen) (the following reaction formula (1)).

Reaction formula (1)

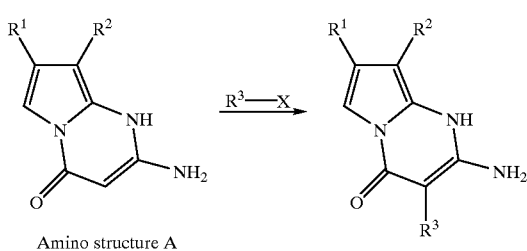

Amino structure A

Further, when R³ is a carbamoyl group, isocyanate can be used Instead of halide as a reaction agent (the following reaction formula (2)).

Reaction formula (2)

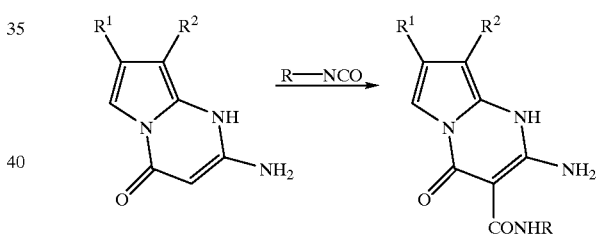

The compound of the present inventioin represented by the general formula (2) can be obtained by first reacting the amino structure A with chlorosulfonylisocyanate or chlorocarbonylssocyanate, to which a base is added thereafter for causing a reaction (see the following reaction formula (3)).

Reaction formula (3)

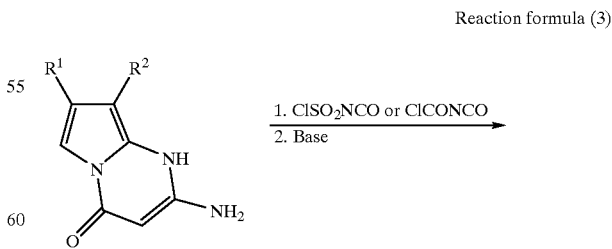

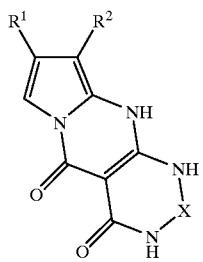

The amount of halide (R³—X) and isocyanate used in the reactions shown in the reaction formulae (1) and (2) is approximately 1 through 10 equivalent and preferably 1 through 5 equivalent in relation to 1 equivalent of the amino structure used as raw material.

As the solvent for dissolving the amino structure A, various types of solvents or a mixture thereof can be used, examples of the solvents including aromatic hydrocarbons such as benzene, toluene and xylene, chain or cyclic aliphatic hydrocarbons such as pentane, hexane, heptane and cyclohexane, ethers such as diethyl ether, duisopropyl ether, tetrahydrofuran, dioxane and ethyleneglycoldimethylether, halogenated hydrocarbons such as dichloromethane, chloroform, 1,2-dichloroethane, nitriles such as acetonitrile, acetic esters such as methyl acetate and ethyl acetate, N,N-dimethylformamide, N,N-dimethylacetamide, dimethylsulfoxide and the like. The amount to be used of the above solvents is not particularly limited.

Examples of a method for running the reactions include a method in which halide or isocyanate is dripped or added in portions into a solution of the amino structure A.

The temperature at which the reactions are run is normally selected from a range of from room temperature to the boiling point of the solvent, and is preferably from 20 through 70° C.

The time of the reactions is normally approximately of from 0.5 through 24 hours, which varies depending on the reaction temperature.

A catalyst may be added to the reactions as needed so as to reduce the reaction time and to improve the yield.

Examples of the catalyst include a boron trifluoride diethyl ether complex, a tin catalyst such as dibutyltindiacetate, aluminum chloride and the like.

The amount of the catalyst to be used is approximately up until 0.5 equivalent and is preferably approximately up until 0.05 equivalent in relation to 1 equivalent of the amino structure A.

After the reactions are completed, the target object can be derived by conventional after-treatment operations such as extraction, and further, refining can be carried out, as needed, by refining means such as silica gel column chromatography and recrystallization.

When the boiling point of the solvent used for the reactions is low, the extracting operation can be omitted and the refining can be carried out after the reaction liquid is concentrated.

The first stage of the reaction shown by the reaction formula (3), in other words, the addition reaction of isocyaniate, can be carried out under the same conditions as the ones shown by the reaction formulae (1) and (2). The generated intermediate is not to be isolated, and the target object can be obtained by treating it with a base (the second stage).

Examples of the base include organic bases such as triethylamine, pyridine and DBU, alkali metal hydrides such as sodium hydride and potassium hydride, metal alcoholates such as sodium methylate, sodium ethylate and potassium butylate, alkali metal hydroxides such as sodium hydroxide and potassium hydroxide, alkaline earth metal hydroxides such as calcium hydroxide and magnesium hydroxide, alkali metal carbonates such as sodium hydrogencarbonate, potassium carbonate and potassium hydrogencarbonate, alkali metallic salts of lower carboxylic acids such as sodium formate and sodium acetate and the like. Of the above bases, organic bases such as triethylamine and pyridine, and alkali metal hydrides such as sodium hydroxide are preferable.

The amount of the base to be used is preferably 1 through 2 equivalent in relation to 1 equivalent of the amino structure A.

The amino structure A used as raw material can be synthesized by the following method described in Japanese Patent Application No. 10-210029. Further, an aminopyrrole derivative can be synthesized by the method described in Japanese Patent Application No. 9-63619 and the like.

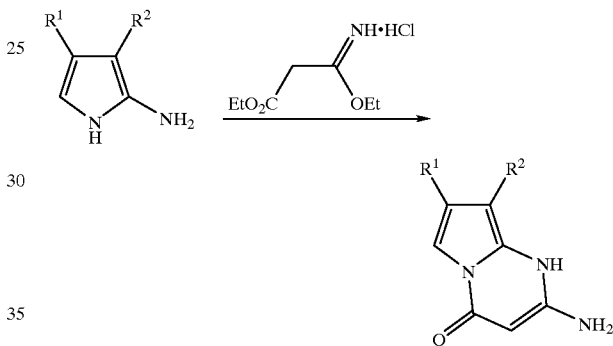

In the general formula (3), $R^{19}$ and $R^{20}$ each independently represents a hydrogen atom, halogen atom, aryl group, alkyl group, cyano group, acyl group, substituted carbamoyl group, alkoxycarbonyl group, aryloxycarbonyl group, acyloxy group, alkoxy group, aryloxy group, alkylthio group, arylthio group, substituted sulfamoyl group, alkylsulfonyl group, arylsulfonyl group, alkylphosphoryl group, arylphosphoryl group, or substituted amino group.

$R^{30}$ and $R^{40}$ each independently represents a hydrogen atom, alkyl group, aryl group, cycloalkyl group, piperidyl group, acyl group, $-C_nH_{2n}N(R^{50})(R^{60})$ or $-C_mH_{2m}XC_lH_{2l}N(R^{70})(R^{80})$.

$R^{50}$ through $R^{80}$ each independently represents a hydrogen atom, alkyl group or aryl group.

X represents an oxygen atom, sulfur atom, or $N(R^{90})-$. $R^{90}$ represents a hydrogen atom, alkyl group or aryl group. $R^{30}$ and $R^{40}$, or $R^{50}$ and $R^{60}$, or $R^{70}$ and $R^{80}$, or $R^{70}$ and $R^{90}$, or $R^{80}$ and $R^{90}$ may combine with each other to form a ring, and in the case of ring formation, they may contain a hetero atom. n, m and l represent integers from 1 through 12.

Of the above values, as the substituents represented by $R^{19}$ and $R^{20}$, at least one of $R^{19}$ and $R^{20}$ is preferably an electron attractive group whose value of Hammett's substituent constant $\sigma_p$ is equal to or larger than 0.20, and it is further preferable that at least one of $R^{19}$ and $R^{20}$ is an electron attractive group whose value of $\sigma_p$ is equal to or larger than 0.35.

Examples of the electron attractive groups whose value of $\sigma_p$ is equal to or larger than 0.20 preferably include, but are not limited to, a cyano group (whose $\sigma_p$ value is 0.66), perfluoroalkyl group (for example, trifluoromethl group whose $\sigma_p$ value is 0.54), acyl group (for example, acetl group whose $\sigma_p$ value is 0.50, benzoyl group whose $\sigma_p$ value is 0.43), carbamoyl group (whose $\sigma_p$ value is 0.36) and the like.

Examples of the halogen atom include a fluorine atom, chlorine atom, bromine atom and the like, and a fluorine atom and chlorine atom are further preferable.

Of the substituents represented by $R^{19}$ and 20, the aryl group may be substituted further by an alkyl group, alkoxy group, aryloxy group, halogen atom, nitro group, cyano group, substituted carbamoyl group, substituted sulfamoyl group, substituted amino group, substituted oxycarbamoyl group, substituted oxysulfonyl group, alkylthio group, arylthio group, alkylsulfonyl group, arylsulfonyl group, aryl group, hydroxy group, acyl group, acyloxy group, substituted sulfonyloxy group, substituted aminocarbonyloxy group, or substituted phosphoryloxy group.

As the aryl group, an aryl group having 6 through 30 carbon atoms is preferable, and examples thereof include not only a phenyl group, 2-methylphenyl group, 2-chlorophenyl group, 2-methoxyphenyl group, 2-ethoxyphenyl group, 2-propoxyphenyl group, 2-isopropoxyphenyl group, 2-butoxyphenyl group, 2-(2-ethylhexyloxy)phenyl group, 2-octyloxyphenyl group, 2-undecyloxyphenyl group, 2-trifluoromethylphenyl group, 2-(2-ethylhexyloxy)-5-chlorophenyl group, 2-(2-ethylhexyloxy)-3,5-dichlorophenyl group, 3-(2,4-di-t-pentylphenoxyethoxy) phenyl group, 2-(dibutylaminocarbonylethoxy)phenyl group, 2,4-dichlorophenyl group, 2,5-dichlorophenyl group, 2,4,6-trimethylphenyl group, 3-chlorophenyl group, 3-nitrophenyl group, 3-cyanophenyl group, 3-trifluoromethylphenyl group, 3-methoxypheny,l group, 3-ethoxyphenyl group, 3-butoxyphenyl group, 3-(2-ethylhexyloxy)phenyl group, 3,4-dichlorophenyl group, 3,5-dichlorophenyl group, 3,4-dimethoxyphenyl group, 3,5-dibutoxyphenyl group, 3-octyloxyphenyl group, 3-(dibutylaminocarbonylmethoxy)phenyl group, 3-(di-2-ethylhexylaminocarbonylmethoxy)phenyl group, 3-dodecyloxyphenyl group, 4-chlorophenyl group, 4-cyanophenyl group, 4-nitrophenyl group, 4-trifluoromethylphenyl group, 4-methoxyphenyl group, 4-ethoxyphenyl group, 4-isopropoxyphenyl group, 4-butoxyphenyl group, 4-(2-ethylhexyloxy)phenyl group, 4-isopentyloxyphenyl group, 4-(octadecyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexyloxycarbonyl)phenyl group, 4-t-octylphenyl group, 4-fluorophenyl group, 3-acetylphenyl group, 2-acetylaminophenyl group, 2,4-di-t-pentylphenyl group, 4-(2-ethylhexyloxy)carbonylphenyl group, 4-methylthiophenyl group and 4-(4-chlorophenylthio) phenyl group, but also hydroxyphenyl group, phenylsulfonylphenyl group, phenylsulfonyloxyphenyl group, phenylcarbonyloxyphenyl group, dimethylaminocarbonyloxyphenyl group, butylcarbonyloxyphenyl group and the like.

Of the substituents represented by $R^{19}$ and $R^{20}$, the alkyl group may be linear or branched, and may have an unsaturated bond. Further, the above alkyl group may be substituted by an alkoxy group, aryloxy group, alkoxycarbonyl group, aryloxycarbonyl group, aryl group, hydroxy group, halogen atom or the like. Likewise, the aryl group described above may further be substituted by an alkyl group, alkoxy group, nitro group, cyano group, hydroxy group or a halogen atom.

As the alkyl group, an alkyl group having 1 through 30 carbon atoms is preferable, and examples thereof include a methyl group, trifluoromethyl group, ethyl group, butyl group, hexyl group, octyl group, 2-ethylhexyl group, decyl group, dodecyl group, octadecyl group, propyl group, isopropyl group, isobutyl group, sec-butyl group, t-butyl group, pentyl group, 1-ethylpentyl group, cyclopentyl group, cyclohexyl group, isopentyl group, heptyl group, nonyl group, undecyl group, propenyl group, heptadecenyl group, t-octyl group, ethoxycarbonylmethyl group, butoxycarbonylmethyl group, 2-ethylhexyloxycarbonylmethyl group, 1-(ethoxycarbonyl)ethyl group, 2',4'-diisopentylphenyloxymethyl group, 2',4'-di-t-butylphenyloxymethyl group, ethoxycarbonylethyl group, 2-ethylhexyloxycarbonylethyl group, butyldecyloxycarbonylethyl group, dibutylaminocarbonylmethyl group, dibenzylaminocarbonylethyl group, ethyloxycarbonylpropyl group, 2-ethylhexyloxycarbonylpropyl group, 2,4-di-t-amylphenyloxypropyl group, 1-(2',4'-di-t-amylphenyloxy) propyl group, 2,4-di-t-butylphenyloxypropyl group, acetylaminoethyl group, N,N-dihexylaminocarbonylethyl group, 2,4-di-t-amyloxyethyloxycarbonylpropyl group, isostearyloxycarbonylpropyl group, 1-(2,4-di-t-pentylphenyloxy) propyl group, 2,4-di-t-pentylphenyloxyethyloxycarbonylpropyl group, naphthyloxyethyloxycarbonylethyl group, N-methyl-N-phenylethyloxycarbonylethyl group, methanesulfonylaminopropyl group and the like.

Of the substituents represented by $R^{19}$ and $R^{20}$, an acyl group having 2 through 20 carbon atoms is preferable as the acyl group, and examples thereof include an acetyl group, propanoyl group, butanoyl group, hexanoyl group, octanoyl group, 2-ethylhexanoyl group, decanoyl group, dodecanoyl group, octadecanoyl group, 2-cyanopropanoyl group, 1,1-dimethylpropanoyl group and the like.

Of the substituents represented by $R^{19}$ and $R^{20}$, the substituted carbamoyl group includes a carbamoyl group, N-alkylcarbamoyl group, N-arylcarbamoyl group, N,N-dialkylcarbamoyl group, N,N-diarylcarbamoyl group, N-alkyl-N-arylcarbamoyl group and the like.

As the substituted carbamoyl group, a substituted carbamoyl group having 1 through 30 carbon atoms is preferable, and examples thereof include an N-methylcarbamoyl group, N-ethylcarbamoyl group, N-propylcarbamoyl group, N-butylcarbamoyl group, N-hexylcarbamoyl group, N-cyclohexylcarbamoyl group, N-octylcarbamoyl group, N-2-ethylhexylcarbamoyl group, N-decylcarbamoyl group, N-octadecylcarbamoyl group, N-phenylcarbamoyl group, N-2-methylphenylcarbamoyl group, N-2-chlorophenylcarbamoyl group, N-2-methoxyphenylcarbamoyl group, N-2-isopropoxyphenylcarbamoyl group, N-2-(2-ethylhexyloxy) phenylcarbamoyl group, N-3-chlorophenylcarbamoyl group, N-3-nitrophenylcarbamoyl group, N-3-cyanophenylcarbamoyl group, N-4-methoxyphenylcarbamoyl group, N-4-(2-ethylhexyloxy) phenylcarbamoyl group, N-4-cyanophenylcarbamoyl group, N-methyl-N-phenylcarbamoyl group, N,N-dimethylcarbamoyl group, N,N-dibutylcarbamoyl group, N,N-diphenylcarbamoyl group and the like.

Of the substituents represented by $R^{19}$ and $R^{20}$, an alkoxycarbonyl group having 2 through 20 carbon atoms is preferable as the alkoxycarbonyl group, and examples thereof include a methoxycarbonyl group, ethoxycarboiyl group, propoxycarbonyl group, butoxycarbonyl group, hexyloxycarbonyl group, 2-ethylhexyloxycarbonyl group, octyloxycarbonyl group, decyloxycarbonyl group, octadecyloxycarbonyl group, phenyloxyethyloxycarbonyl group, phenyloxypropyloxycarbonyl group, 2,4-di-t-amylphenyloxyethylcarbonyl group, 2,6-di-t-butyl-4-methylcyclohexyloxycarbonyl group, isostearyloxycarbonyl group and the like.

Of the substituents represented by $R^{19}$ and $R^{20}$, an aryloxycarbonyl group having 7 through 30 carbon atoms is preferable as the aryloxycarbonyl group, and examples thereof include a 2-methylphenyloxycarbonyl group, 2-chlorophenyloxycarbonyl group, 2,6-dimethylphenyloxycarbonyl group, 2,4,6-trimethylphenyloxycarbonyl group, 2-methoxyphenyloxycarbonyl group, 2-butoxyphenyloxycarbonyl group, 3-cyanophenyloxycarbonyl group, 3-nitrophenyloxycarbonyl group, 2,2-ethylhexylphenyloxycarbonyl group, 3-(2-ethylhexyloxy)phenyloxycarbonyl group, 4-fluorophenyloxycarbonyl group, 4-chlorophenyloxycarbonyl group, 4-cyanophenyloxycarbonyl group, 4-butoxyphenyloxycarbonyl group and the like.

Of the substituents represented by $R^{19}$ and $R^{20}$, an acyloxy group having 2 through 20 carbon atoms is preferable as the acyloxy group, and examples thereof include an acetyloxy group, propanoyloxy group, butanoyloxy group, pentanoyloxy group, trifluoromethylcarbonyloxy group, octanoyloxy group, decanoyloxy group, undecanoyloxy group, octadecanoyloxy group and the like.

Of the substituents represented by $R^{11}$ and $R^{20}$, an alkoxy group having 1 through 30 carbon atoms is preferable as the alkoxy group, and examples thereof include a methoxy group, ethoxy group, propyloxy group, isopropyloxy group, butoxy group, isobutoxy group, sec-butoxy group, t-butoxy group, pentyloxy group, isopenty,loxy group, hexyloxy group, heptnloxy group, octyloxy group, 2-ethylhexyloxy group, decyloxy group, dodecyloxy group, octadecyloxy group, ethoxycarbonylmethyloxy group, 2-ethylhexyloxycarbonylmethyloxy group, aminocarbonylmethyloxy group, N,N-dibutylaminocarbonylmethyloxy group, N-methylaminocarbonylmethyloxy group, N-ethylaminocarbonylmethyloxy group, N-octylaminocarbonylmethyloxy group, N-methyl-N-benzylaminocarbonylmethyloxy group, benzyloxy group, cyanomethyloxy group and the like.

Of the substituents represented by $R^{19}$ and $R^{20}$, an aryloxy group having 6 through 30 carbon atoms is preferable as the aryloxy group, and examples thereof include a phenyloxy group, 1-naphthyloxy group, 2-naphthyloxy group, 2-chlorophenyloxy group, 2-methylphenyloxy group, 2-methoxyphenyloxy group, 2-butoxyphenyloxy group, 3-chlorophenyloxy group, 3-trifluoromethlphenyloxy group, 3-cyanophenyloxy group, 3-(2-ethylhexyloxy)phenyloxy group, 3-nitrophenyloxy group, 4-fluorophenyloxy group, 4-cyanophenyloxy group, 4-butoxyphenyloxy group, 4-(2-ethylhexyloxy)phenyloxy group, 4-octadecylphenyloxy group and the like.

Of the substituents represented by $R^{19}$ and $R^{20}$, an alkylthio group having 1 through 30 carbon atoms is preferable as the alkylthio group, and examples thereof include a methylthio group, ethylthio group, propylthio group, isopropylthio group, butylthio group, isobutylthio group, sec-butyl thio group, t-butylthio group, pentylthio group, isopentylthio group, hexylthio group, heptylthio group, octylthio group, 2-ethylhexylthio group, decylthio group, dodecylthio group, octadecylthio group, ethox ycarbonylmethio group, 2-ethyilhexyloxycarbonylmethylthio gcroup, aminocarbonylmethylthio group, N,N-dibutylamimiocarboonylmethylthlio group, N-methylaminocarbonylmethylthio group, N-ethylaminocarbonylmethylthio group, N-octylaminocarbonylmethylthio group, N-methyl-N-benzylaminocarbonylmethylthio group, benzylthio group, cyanomethylthio group and the like.

Of the substituents represented by $R^{19}$ and $R^{20}$, an arylthio group having 6 through 30 carbon atoms is preferable as the arylthio group, and examples thereof include a phenylthio group, 1-naphthylthio group, 2-naphthylthio group, 2-chlorophenylthio group, 2-methylphenylthio group, 2-methoxyphenylthio group, 2-butoxyphenylthio group, 3-chlorophenylthio group, 3-trifluoromethlphenylthio group, 3-cyanophenylthio group, 3-(2-ethylhexyloxy)phenylthio group, 3-nitrophenylthio group, 4-fluorophenylthio group, 4-cyanophenylthio group, 4-butoxyphenylthio group, 4-(2-ethylhexyloxy)phenylthio group, 4-octadecylphenylthio group and the like.

Of the substituents represented by $R^{19}$ and $R^{20}$, the substituted sulfamoyl group includes a sulfamoyl group, N-alkylsulfamoyl group, N-arylsulfamoyl group, N,N-dialkylsulfamoyl group, N,N-diarylsulfamoyl group, N-alkyl-N-arylsulfamoyl group and the like.

Of the substituents represented by $R^{19}$ and $R^{20}$, a substituted sulfamoyl group having 0 through 30 carbon atoms is preferable as the substituted sulfamoyl group, and examples thereof include an N-methylsulfamoyl group, N-ethylsulfamoyl group, N-propylsulfamoyl group, N-butylsulfamoyl group, N-hexylsulfamoyl group, N-cyclohexylsulfamoyl group, N-octylsulfamoyl group, N-2-ethylhexylsulfamoyrl group, N-decylsulfamoyl group, N-octadecylsulfamoyl group, N-phenylsulfamoyl group, N-2-methylphenylsulfamol group, N-2-chlorophenylsulfamoyl group, N-9-methoxyphenylsulfamoyl group, N-2-isopropoxyphenylsulfamoyl group, N-2-(2-ethylhexyloxy)phenylsulfamoyl group, N-3-chlorophenylsulfamoyl group, N-3-nitrophenylsulfamoyl group, N-3-cyanophenylsulfamoyl group, N-4-methoxysulfamoyl group, N-4-(2-ethylhexyloxy)phenylsulfamoyl group, N-4-cyanophenylsulfamoyl group, N-methyl-N-phenylsulfamoyl group, N,N-dimethylsulfamoyl group, N,N-dibutylsulfamoyl group, N,N-diphenylsulfamoyl group, N,N-di-(2-ethylhexyl)sulfamoyl group and the like.

Of the substituents represented by $R^{19}$ and $R^{20}$, an alkylsulfonyl group having 1 through 20 carbon atoms is preferable as the alkylsulfonyl group, and examples thereof include a methylsulfonyl group, ethylsulfonyl group, propylsulfonyl group, isopropylsulfonyl group, butylsulfonyl group, hexylsulfonyl group, cyclohexylsulfonyl group, octylsulfonyl group, 2-ethylhexylsulfonyl group, decanoylsulfonyl group, dodecanoylsulfonyl group, octadecanoylsulfonyl group, cyanomethylsulfonyl group and the like.

Of the substituents represented by $R^{19}$ and $R^{20}$, an arylsulfonyl group having 6 through 30 carbon atoms is preferable as the arylsulfonyl group, and examples thereof include a phenylsulfonyl group, 1-naphthylsulfonyl group, 2-naphthylsulfonyl group, 2-chlorophenylsulfonyl group, 2-methylphenylsulfonyl group, 2-methoxyphenylsulfonyl group, 2-butoxyphenylsulfonyl group, 3-chlorophenylsulfonyl group, 3-trifluoromethylphenylsulfonyl group, 3-cyanophenylsulfonyl group, 3-(2-ethylhexyloxy)phenylsulfonyl group, 3-nitrophenylsulfonyl group, 4-fluorophenylsulfonyl group, 4-cyanophenylsulfonyl group, 4-butoxyphenylsulfonyl group, 4-(2-ethylhexyloxy) phenylsulfonyl group, 4-octadecylphenylsulfonyl group and the like.

Of the substituents represented by $R^{19}$ and $R^{20}$, an alkylphosphoryl group having 2 through 40 carbon atoms is preferable as the alkylphosphoryl group, and examples thereof include a methylphosphoryl group, ethylphosphoryl group, propylphosphoryl group, isopropylphosphoryl group, butylphosphoryl group, isobutylphosphoryl group, sec-butylphosphoryl group, t-butylphosphoryl group, pentylphosphoryl group, isopentylphosphoryl group, hexylphosphoryl group, heptylphosphoryl group, octylphosphoryl group, 2-ethylhexylphosphoryl group, decylphosphoryl group, dodecylphosphoryl group, octadecylphosphoryl group, ethoxycarbonylmethylphosphoryl group, 2-ethylhexyloxycarbonylmethylphosphoryl group, aminocarbonylmethylphosphoryl group, N,N-dibutylaminocarbonylmethylphosphoryl group, N-methylaminocarbonylmethylphosphoryl group, N-ethylaminocarbonylmethylphosphoryl group, N-octylaminocarbonylmethylphosphoryl group, benzylphosphoryl group and the like.

Of the substituents represented by $R^{19}$ and $R^{20}$, an arylphosphoryl group having 12 through 50 carbon atoms is preferable as the arylphosphoryl group, and examples thereof include a phenylphosphoryl group, 1-naphthylphosphoryl group, 2-naphthylphosphoryl group, 2-chlorophenylphosphoryl group, 2-methylphenylphosphoryl group, 2-methoxyphenylphosphoryl group, 2-butoxyphenylphosphoryl group, 3-chlorophenylphosphoryl group, 3-trifluoromethylphenylphosphoryl group, 3-cyanophenylphosphoryl group, 3-(2-ethylhexyloxy) phenylphosphoryl group, 3-nitrophenylphosphoryl group, 4-fluorophenylphosphoryl group, 4-cyanophenylphosphoryl group, 4-butoxyphenylphosphoryl group, 4-(2-ethylhexyloxy)phenylphosphoryl group, 4-octadecylphenylphosphoryl group and the like.

Of the substituents represented by $R^{19}$ and $R^{20}$, the substituted amino group includes an amino group, N-alk7lamino group, N-arylamino group, N-acylamino group, N-sulfonylamino group, N,N-dialkylamino group, N,N-diarylamino group, N-alkyl-N-arylamino group, N,N-disulfonylamino group and the like.

As the substituted amino group, a substituted amino group having 0 through 50 carbon atoms is preferable, and examples thereof include an N-methylamino group, N-ethylamino group, N-propylamino group, N-isopropylamino group, N-tert-butylamino group, N-hexylamino group, N-cyclohexylamino group, N-octylamino group, N-2-ethylhexylamino group, N-decylamino group, N-octadecylamino group, N-benzylamino group, N-phenylamino group, N-2-methylphenylamino group, N-2-chlorophenylamino group, N-2-methoxyphenylamino group, N-2-isopropoxyphenylamino group, N-2-(2-ethylhexyloxy) phenylamino group, N-3-chlorophenylamino group, N-3-nitrophenylamino group, N-3-cyanophenylamino group, N-4-methoxyamino group, N-4-(2-ethylhexyloxy) phenylamino group, N-4-cyanophenylamino group, N-methyl-N-phenylamino group, N,N-dimethylamino group, N,N-dibutylamino group, N,N-diphenylamino group, N,N-diacetylamino group, N,N-dibenzoylamino group, N,N-(dibutylcarbonyl)amino group, N,N-(di-2-ethylhexyl1carbonyl)amino group, N,N-(dimethylsulfonyl) amino group, N,N-(diethylsulfonyl)amino group, N,N-(dibutylsulfonyl)amino group, N,N-(2-ethylhexylsulfonyl) amino group, N,N-(diphenylsulfonyl)amino group and the like.

Of the substituents represented by $R^{30}$ and $R^{40}$, an alkyl group, aryl group and acyl group may have the same contents as those of the alkyl group, aryl group and acyl group explained above for $R^{19}$ and $R^{20}$. Further, of the substituents represented by $R^{30}$ and $R^{40}$, a cycloalkyl group having 3 through 12 carbon atoms, which may have furthermore substituents, is preferable as the cycloalkyl group, and examples thereof include a substituted or unsubstituted cyclopentane, cyclohexane, cycloheptane and the like. Likewise, of the substituents represented by $R^{30}$ and $R^{40}$, a piperidyl group includes the ones expressed by the following formulae.

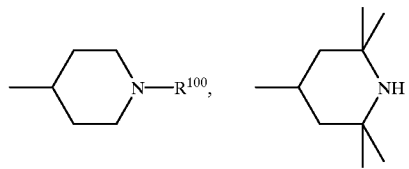

In the above formula, $R^{100}$ represents an alkyl group having 1 through 4 carbon atoms.

Of the substituents represented by $R^{30}$ and $R^{40}$, $R^{50}$ through $R^{80}$ of the substituents expressed by $-C_nH_{2n}N(R^{50})(R^{60})$ or $-C_mH_{2m}XC_lH_{2l}N(R^{70})(R^{80})$ represents a hydrogen atom, alkyl group or an aryl group that may have substituents. As the alkyl group, an alkyl group having 1 through 8 carbon atoms is preferable, and as the aryl group, a phenyl group is preferable. In the formula, X represents an oxygen atom, sulfur atom, or $N(R^{90})$. $R^{90}$ represents a hydrogen atom, an alkyl group or an aryl group that may have substituents, and of the above substituents, an alkyl group having 1 through 4 carbon atoms, and a phenyl group are preferable. Further, in the formula, m, n and l represent integers from 1 through 12, and 2 through 4 are preferable. Likewise, the combined group represented by $C_nH_{2n}$, $C_mH_{2m}$ and $C_lH_{2l}$ in the two formulae may be linear or branched, and examples of the structure thereof include the following formulae.

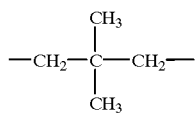

Further, rings that can be formed by $R^{30}$ and $R^{40}$, or $R^{50}$ and $R^{60}$, or $R^{70}$ and $R^{80}$, or $R^{70}$ and $R^{90}$, or $R^{80}$ and $R^{90}$ include the following rings and the like.

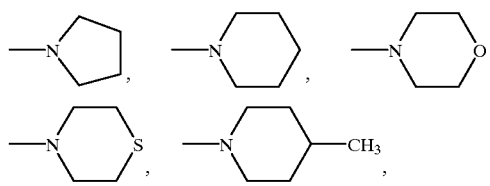

-continued

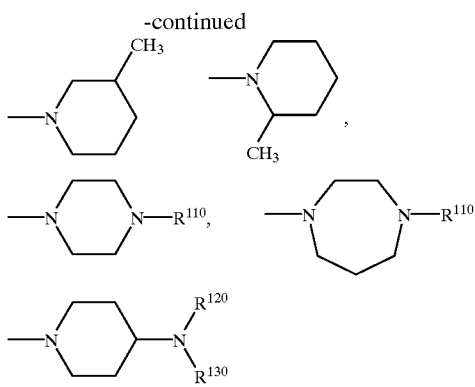

In the above formulae, $R^{110}$ through $R^{130}$ each independently represents a hydrogen atom, an alkyl group, aryl group or acyl group. Of the above, an alkl group having 1 through 4 carbon atoms is preferable.

Next, a description will given of a synthesizing method of the pyrrolo[1,2-a]pyrimidine compound represented by the general formula (3). The pyrrolo[1,2-a]pyrimidine compound represented by the general formula (3) can be synthesized, for example, by following the formula given below.

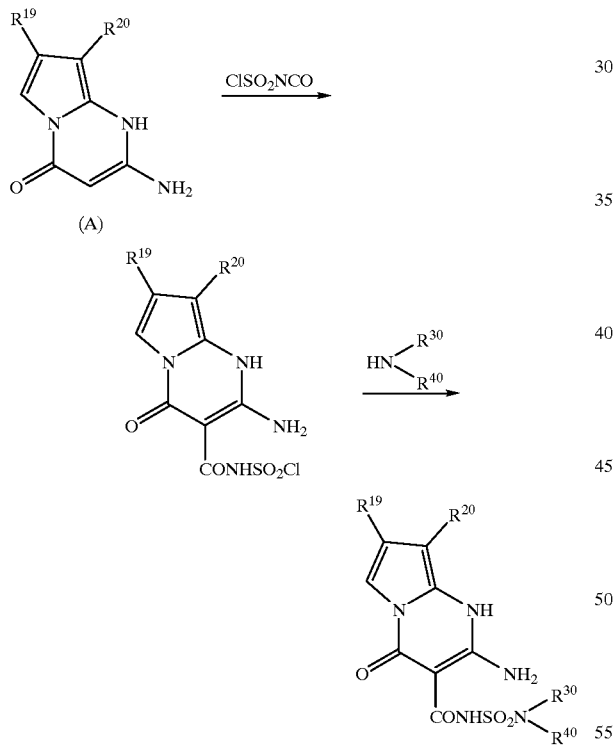

$R^{19}$, $R^{20}$, $R^{30}$ and $R^{40}$ in the reaction formula have the same meanings as those in the general formula (3), respectively.

The pyrrolo[1,2-a]pyrimidine compound represented by the above general formula (3) can be obtained by first reacting the compound (A) (the amino structure) with chlorosulfonylisocyanate, to which $HN(R^{30})(R^{40})$ is added thereafter for causing a reaction.

In the reactions represented by the above scheme, at the first stage for an addition reaction with chlorosulfonylisocyanate, the amount of chlorosulfonylisocyanate used is 0.9 through 2.5 equivalent and preferably 1.1 through 1.6 equivalent in relation to the compound (A) used as raw material.

As the solvent for use in the reaction, various types of solvents that are inert to chlorosulfonylisocyanate and a mixture thereof can be used, examples of the solvents including aromatic hydrocarbons such as benzene, toluene and xylene, chain or cyclic aliphatic hydrocarbons such as pentane, hexane, heptane and cyclohexane, ethers such as diethyl ether, diisopropyl ether, tetrahydrofuran and ethyleneglycoldimethylether, halogenated hydrocarbons such as dichloromethane, chloroform, 1,2-dichloroethane, nitrites such as acetonitrile and the like. Of the above solvents, acetonitrile and tetrahydrofuran are preferable. The amount to be used of the above solvents is not particularly limited.

Examples of a method for running the reaction include a method in which chlorosulfonylisocyanate is dripped into a solution of (A).

The temperature at which the reaction is run is approximately from −40 through 40° C., and is preferably from −15 through 25° C.

The time of the reaction is normally approximately from 0.5 through 24 hours, which varies depending on the temperature of the reaction.

Subsequently, the second stage, i.e., the reaction with $HN(R^{30})(R^{40})$, can be carried out without treating the addition reaction liquid of chlorosulfonylisocyanate.

The amount of $HN(R^{30})(R^{40})$ to be used is 1.8 through 4.0 equivalent, and is preferably 1.8 through 3.0 equivalent, in relation to the compound (A) used as raw material.

The temperature at which the reaction in the second stage is run is approximately from −40 through 40° C., and is preferably from −25 through 40° C. The time of the reaction at the second stage is normally from 0.5 through 24 hours, which varies depending on the reaction temperature.

The compound (A) used as raw material can be synthesized by a method described in Japanese Patent Application No. 10-210029.

Here, specific examples of the pyrrolo[1,2-a]pyrimidine compound represented by the general formula (3) are given. However, the pyrrolo[1,2-a]pyrimidine compound of the present invention is not limited to the following examples. The following are examples of substituents represented by $R^{19}$, $R^{20}$, $R^{30}$ and $R^{40}$ in the general formula (3). Further, specific examples of compounds in which the above substituents are combined are shown in Tables 8 through 16.

(1) —H (2) —CH₃

(3) —C₆H₅

(4) —C₆H₄—Cl (5) 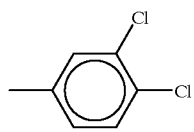
(6) 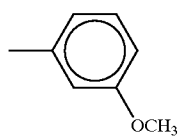
(7) 
—CN
(8) 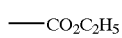
—CO₂C₂H₅
(9) 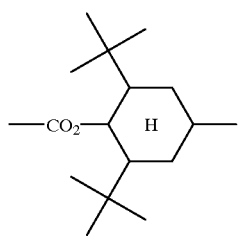
(10) 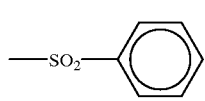
—SO₂CH₃
(11) 
(12) —CONHC₈H₁₇
(13) 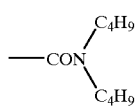
(14) 
—C₂H₅
(15) 
—C₄H₉
(16) 
—C₆H₁₃
(17) 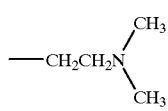
(18) 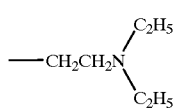
(19) 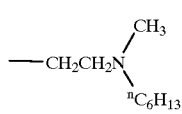
(20) 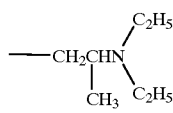
(21) 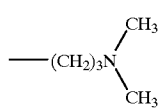
(22) 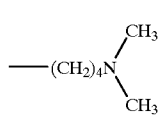
(23) 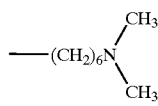
(24) 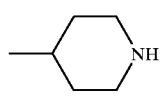
(25) 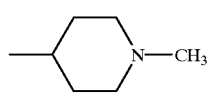
(26) 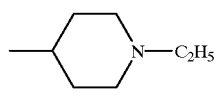
(27) 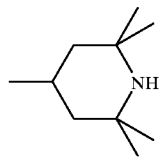
(28) 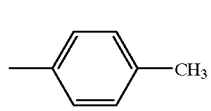
(29) 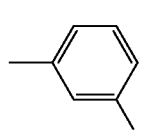
(30) 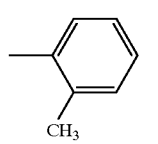

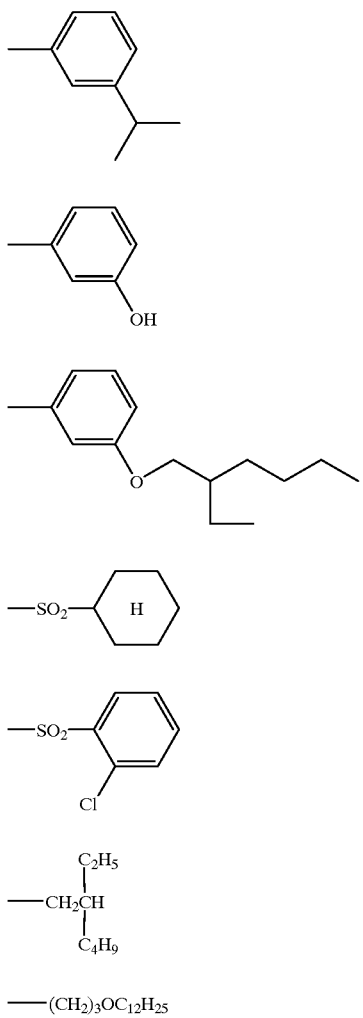
(31)
(32)
(33)
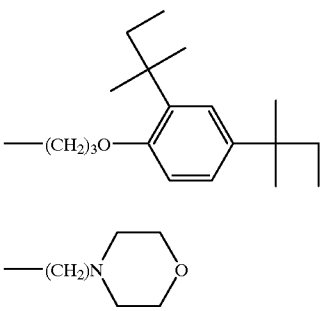
(38)
(39)
Examples of rings that are formed by $R^{30}$ and $R^{40}$, or $R^{50}$ and $R^{60}$, or $R^{70}$ and $R^{80}$, or $R^{70}$ and $R^{90}$, or $R^{80}$ and $R^{90}$ include the following rings.
(34)
(A)
(35)
(B)
(36)
(C)
(37)
(D)
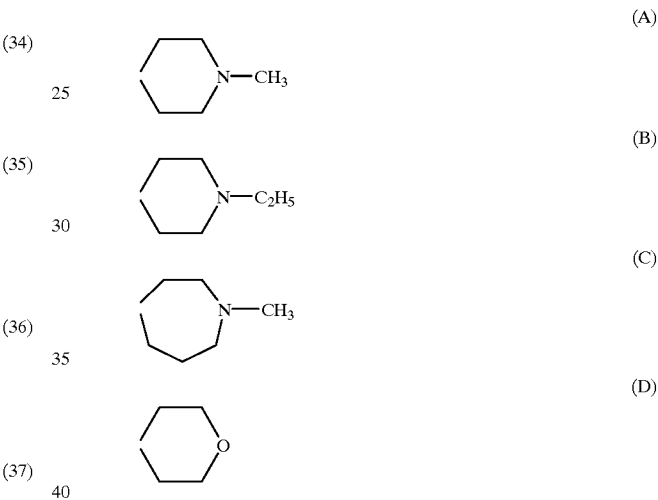
TABLE 8
| Coupler No. | $R^{19}$ | $R^{20}$ | $R^{30}$ | $R^{40}$ |
|---|---|---|---|---|
| (1) | —⌬ | —CN | —H | —CH$_2$CH$_2$N(CH$_3$)(CH$_3$) |
| (2) | —⌬ | —CN | —H | —CH$_2$CH$_2$N(CH$_3$)(nC$_6$H$_{13}$) |
| (3) | —⌬ | —CN | —H | —(CH$_2$)$_6$N(CH$_3$)(CH$_3$) |
| (4) | —⌬ | —CN | —CH$_3$ | —CH$_2$CH$_2$N(CH$_3$)(CH$_3$) |

TABLE 8-continued

| Coupler No. | $R^{19}$ | $R^{20}$ | $R^{30}$ | $R^{40}$ |
|---|---|---|---|---|
| (5) | phenyl | —CN | —C$_2$H$_5$ | —CH$_2$CH$_2$N(C$_2$H$_5$)$_2$ |
| (6) | phenyl | —CN | —C$_6$H$_{13}$ | 4-piperidinyl (NH) |
| (7) | phenyl | —CN | —C$_2$H$_5$ | 1-methyl-4-piperidinyl |
| (8) | phenyl | —CN | —C$_4$H$_9$ | 2,2,6,6-tetramethyl-4-piperidinyl (NH) |
| (9) | phenyl | —CN | | 1-methylpiperidin-1-yl |
| (10) | —CH$_3$ | —CN | | 1-ethylpiperidin-1-yl |

TABLE 9

| Coupler No. | $R^{19}$ | $R^{20}$ | $R^{30}$ | $R^{40}$ |
|---|---|---|---|---|
| (11) | —H | —CN | —C$_6$H$_{13}$ | —CH$_2$CH$_2$N(CH$_3$)$_2$ |
| (12) | —CH$_3$ | —CN | —H | —CH$_2$CH$_2$N(CH$_3$)$_2$ |
| (13) | —CH$_3$ | —CN | —C$_2$H$_5$ | —CH$_2$CH$_2$N(C$_2$H$_5$)$_2$ |
| (14) | —CH$_3$ | —CN | —H | —CH$_2$CH(CH$_3$)N(C$_2$H$_5$)$_2$ |
| (15) | —CH$_3$ | —CN | | 1-ethylpiperidin-1-yl |
| (16) | 4-chlorophenyl | —CN | —H | —CH$_2$CH$_2$N(CH$_3$)$_2$ |

TABLE 9-continued

| Coupler No. | $R^{19}$ | $R^{20}$ | $R^{30}$ | $R^{40}$ |
|---|---|---|---|---|
| (17) | 3,4-dichlorophenyl | —CN | —CH$_3$ | —CH$_2$CH$_2$N(CH$_3$)$_2$ |
| (18) | 3-methoxyphenyl | —CN | —C$_2$H$_5$ | —CH$_2$CH$_2$N(C$_2$H$_5$)$_2$ |
| (19) | —CN | —CN | —C$_4$H$_9$ | —CH$_2$CH$_2$N(CH$_3$)$_2$ |
| (20) | phenyl | —CN | | N-methylhexahydroazepinyl |

TABLE 10

| Coupler No. | $R^{19}$ | $R^{20}$ | $R^{30}$ | $R^{40}$ |
|---|---|---|---|---|
| (21) | phenyl | —CN | —CH$_2$CH(C$_2$H$_5$)C$_4$H$_9$ | —CH$_2$CH(C$_2$H$_5$)C$_4$H$_9$ |
| (22) | phenyl | —CN | —CH$_3$ | phenyl |
| (23) | phenyl | —CN | —C$_4$H$_9$ | phenyl |
| (24) | phenyl | —CN | —C$_4$H$_9$ | —C$_4$H$_9$ |
| (25) | phenyl | —CN | —CH$_3$ | 3-methylphenyl |
| (26) | 4-chlorophenyl | —CN | —C$_6$H$_{13}$ | —C$_6$H$_{13}$ |

TABLE 10-continued

| Coupler No. | $R^{19}$ | $R^{20}$ | $R^{30}$ | $R^{40}$ |
|---|---|---|---|---|
| (27) | 4-chlorophenyl | —CN | —H | —(CH$_2$)$_3$O-(2,4-di-tert-butylphenyl) |
| (28) | phenyl | —CN | —H | —(CH$_2$)$_3$OC$_{12}$H$_{25}$ |
| (29) | phenyl | —CN | —H | phenyl |
| (30) | phenyl | —CN | —H | 3-isopropylphenyl |

TABLE 11

| Coupler No. | $R^{19}$ | $R^{20}$ | $R^{30}$ | $R^{40}$ |
|---|---|---|---|---|
| (31) | phenyl | —SO$_2$-phenyl | —H | —CH$_2$CH$_2$N(CH$_3$)$_2$ |
| (32) | phenyl | —SO$_2$-phenyl | —H | —(CH$_2$)$_3$N(CH$_3$)$_2$ |
| (33) | phenyl | —SO$_2$-phenyl | —H | —(CH$_2$)-morpholino |
| (34) | phenyl | —SO$_2$-phenyl | —CH$_3$ | —CH$_2$CH$_2$N(CH$_3$)$_2$ |
| (35) | 4-chlorophenyl | —SO$_2$-phenyl | —C$_2$H$_5$ | —CH$_2$CH$_2$N(C$_2$H$_5$)$_2$ |
| (36) | phenyl | —SO$_2$-cyclohexyl | —CH$_3$ | —CH$_2$CH$_2$N(CH$_3$)$_2$ |
| (37) | phenyl | —SO$_2$-cyclohexyl | —C$_2$H$_5$ | —CH$_2$CH$_2$N(C$_2$H$_5$)$_2$ |

TABLE 11-continued

| Coupler No. | $R^{19}$ | $R^{20}$ | $R^{30}$ | $R^{40}$ |
|---|---|---|---|---|
| (38) | 4-chlorophenyl- | $-SO_2-$cyclohexyl | $-H$ | $-CH_2CH_2N(CH_3)_2$ |
| (39) | phenyl- | $-SO_2CH_3$ | $-H$ | $-(CH_2)_3O-$(2,4-di-tert-amylphenyl) |
| (40) | phenyl- | $-SO_2-$(2-chlorophenyl) | $-CH_3$ | $-CH_2CH_2N(CH_3)_2$ |

TABLE 12

| Coupler No. | $R^{19}$ | $R^{20}$ | $R^{30}$ | $R^{40}$ |
|---|---|---|---|---|
| (41) | phenyl- | $-SO_2-$phenyl | | N-methylpiperidinyl |
| (42) | phenyl- | $-SO_2-$phenyl | | N-methylhexahydroazepinyl |
| (43) | phenyl- | $-SO_2-$phenyl | $-CH_2CH(C_2H_5)(C_4H_9)$ | $-CH_2CH(C_2H_5)(C_4H_9)$ |
| (44) | phenyl- | $-SO_2-$phenyl | $-H$ | phenyl- |
| (45) | phenyl- | $-SO_2-$phenyl | $-CH_3$ | $-CH_3$ |
| (46) | 4-chlorophenyl- | $-SO_2-$cyclohexyl | $-CH_3$ | 3-methylphenyl- |

TABLE 12-continued

| Coupler No. | $R^{19}$ | $R^{20}$ | $R^{30}$ | $R^{40}$ |
|---|---|---|---|---|
| (47) | phenyl | $-SO_2-$(2-chlorophenyl) | $-H$ | $-(CH_2)_3O-$(2,4-di-tert-pentylphenyl) |
| (48) | 4-chlorophenyl | $-SO_2-$(2-chlorophenyl) | $-C_6H_{13}$ | $-C_6H_{13}$ |
| (49) | 4-chlorophenyl | $-SO_2-$(2-chlorophenyl) | | tetrahydropyranyl |
| (50) | 4-chlorophenyl | $-CO_2-$(2,6-di-tert-butyl-4-methylcyclohexyl) | $-H$ | $-CH_2CH_2N(CH_3)_2$ |

TABLE 13

| Coupler No. | $R^{19}$ | $R^{20}$ | $R^{30}$ | $R^{40}$ |
|---|---|---|---|---|
| (51) | 4-chlorophenyl | $-CO_2-$(2,6-di-tert-butyl-4-methylcyclohexyl) | $-H$ | $-CH_2CH_2N(CH_3)(^nC_6H_{13})$ |
| (52) | 3,4-dichlorophenyl | $-CO_2-$(2,6-di-tert-butyl-4-methylcyclohexyl) | $-H$ | $-CH_2CH_2N(CH_3)_2$ |

TABLE 13-continued

| Coupler No. | $R^{19}$ | $R^{20}$ | $R^{30}$ | $R^{40}$ |
|---|---|---|---|---|
| (53) | 3,4-dichlorophenyl- | -CO$_2$-(2,6-di-tert-butyl-4-methylcyclohexyl) | -H | -CH$_2$CH$_2$N(CH$_3$)(nC$_6$H$_{13}$) |
| (54) | 4-chlorophenyl- | -CO$_2$-(2,6-di-tert-butyl-4-methylcyclohexyl) | -CH$_3$ | -CH$_2$CH$_2$N(CH$_3$)$_2$ |
| (55) | 4-chlorophenyl- | -CO$_2$-(2,6-di-tert-butyl-4-methylcyclohexyl) | -C$_2$H$_5$ | -CH$_2$CH$_2$N(C$_2$H$_5$)$_2$ |
| (56) | 4-chlorophenyl- | -CO$_2$C$_2$H$_5$ | -H | -CH$_2$CH$_2$N(CH$_3$)$_2$ |
| (57) | 3,4-dichlorophenyl- | -CO$_2$C$_2$H$_5$ | -H | -CH$_2$CH$_2$N(C$_2$H$_5$)$_2$ |
| (58) | 3,4-dichlorophenyl- | -CO$_2$-(2,6-di-tert-butyl-4-methylcyclohexyl) | -CH$_3$ | -CH$_2$CH$_2$N(CH$_3$)$_2$ |
| (59) | 3,4-dichlorophenyl- | -CO$_2$-(2,6-di-tert-butyl-4-methylcyclohexyl) | -C$_2$H$_5$ | -CH$_2$CH$_2$N(C$_2$H$_5$)$_2$ |

TABLE 13-continued

| Coupler No. | $R^{19}$ | $R^{20}$ | $R^{30}$ | $R^{40}$ |
| --- | --- | --- | --- | --- |
| (60) | 3,4-dichlorophenyl | —CO$_2$—(2,6-di-tert-butyl-4-methylcyclohexyl, H) | | N-methylpiperidinyl |

TABLE 14

| Coupler No. | $R^{19}$ | $R^{20}$ | $R^{30}$ | $R^{40}$ |
| --- | --- | --- | --- | --- |
| (61) | 4-chlorophenyl | —CO$_2$—(2,6-di-tert-butyl-4-methylcyclohexyl, H) | | N-methylhexahydroazepinyl |
| (62) | 4-chlorophenyl | —CO$_2$C$_2$H$_5$ | | N-methylhexahydroazepinyl |
| (63) | 4-chlorophenyl | —CO$_2$C$_2$H$_5$ | —CH$_3$ | 4-(N-methylpiperidinyl) |
| (64) | 4-chlorophenyl | —CO$_2$C$_2$H$_5$ | —H | —(CH$_2$)$_6$N(CH$_3$)$_2$ |
| (65) | 4-chlorophenyl | —CO$_2$C$_2$H$_5$ | —H | —(CH$_2$)$_3$N(CH$_3$)$_2$ |
| (66) | 4-chlorophenyl | —CO$_2$—(2,6-di-tert-butyl-4-methylcyclohexyl, H) | —CH$_3$ | phenyl |

TABLE 14-continued

| Coupler No. | $R^{19}$ | $R^{20}$ | $R^{30}$ | $R^{40}$ |
|---|---|---|---|---|
| (67) | 4-chlorophenyl | 2,6-di-tert-butyl-4-methylcyclohexyl carboxylate | —H | phenyl |
| (68) | phenyl | —$CO_2C_2H_5$ | —$CH_3$ | phenyl |
| (69) | phenyl | —$CO_2C_2H_5$ | —H | 3-isopropylphenyl |
| (70) | 4-chlorophenyl | 2,6-di-tert-butyl-4-methylcyclohexyl carboxylate | —H | 3-hydroxyphenyl |

TABLE 15

| Coupler No. | $R^{19}$ | $R^{20}$ | $R^{30}$ | $R^{40}$ |
|---|---|---|---|---|
| (71) | 4-chlorophenyl | 2,6-di-tert-butyl-4-methylcyclohexyl carboxylate | —$CH_3$ | 3-hydroxyphenyl |
| (72) | 4-chlorophenyl | 2,6-di-tert-butyl-4-methylcyclohexyl carboxylate | | tetrahydropyranyl |

TABLE 15-continued

| Coupler No. | $R^{19}$ | $R^{20}$ | $R^{30}$ | $R^{40}$ |
|---|---|---|---|---|
| (73) | 3,4-dichlorophenyl | —CO$_2$—(2,6-di-tert-butyl-4-methylcyclohexyl) | | tetrahydropyran-yl |
| (74) | 4-chlorophenyl | —CO$_2$C$_2$H$_5$ | —CH$_2$CH(C$_2$H$_5$)(C$_4$H$_9$) | —CH$_2$CH(C$_2$H$_5$)(C$_4$H$_9$) |
| (75) | 4-chlorophenyl | —CO$_2$C$_2$H$_5$ | —H | —(CH$_2$)$_3$O-(2,4-di-tert-amylphenyl) |
| (76) | 3,4-dichlorophenyl | —CO$_2$C$_2$H$_5$ | —CH$_3$ | 3-methylphenoxy-2-ethylhexyl |
| (77) | 4-chlorophenyl | —CO$_2$—(2,6-di-tert-butyl-4-methylcyclohexyl) | —CH$_3$ | 3,5-dimethylphenyl |
| (78) | 4-chlorophenyl | —CO$_2$—(2,6-di-tert-butyl-4-methylcyclohexyl) | —H | 3,5-dimethylphenyl |
| (79) | 3,4-dichlorophenyl | —CONHC$_8$H$_{17}$ | —CH$_3$ | —CH$_2$CH$_2$N(CH$_3$)$_2$ |

TABLE 15-continued

| Coupler No. | $R^{19}$ | $R^{20}$ | $R^{30}$ | $R^{40}$ |
|---|---|---|---|---|
| (80) | 2,3-dichlorophenyl | —CONHC$_8$H$_{17}$ | —C$_2$H$_5$ | —CH$_2$CH$_2$N(C$_2$H$_5$)$_2$ |

TABLE 16

| Coupler No. | $R^{19}$ | $R^{20}$ | $R^{30}$ | $R^{40}$ |
|---|---|---|---|---|
| (81) | 2,3-dichlorophenyl | —CON(C$_4$H$_9$)$_2$ | | N-methylhexahydroazepine |
| (82) | 2,3-dichlorophenyl | —CON(C$_4$H$_9$)$_2$ | | N-methylpiperidine |
| (83) | 2,3-dichlorophenyl | —CONHC$_8$H$_{17}$ | —CH$_3$ | phenyl |
| (84) | 2,3-dichlorophenyl | —CONHC$_8$H$_{17}$ | —H | phenyl |
| (85) | 4-chlorophenyl | —CONHC$_8$H$_{17}$ | —C$_4$H$_9$ | —C$_4$H$_9$ |
| (86) | 2,3-dichlorophenyl | —CON(C$_4$H$_9$)$_2$ | | morpholine |

Next, the heat-sensitive recording material of the present invention will be described in detail.

The heat-sensitive recording material of the present invention comprises a substrate on which a heat-sensitive recording layer is provided. Further, the heat-sensitive recording material may include other layers if needed.

Heat-sensitive Recording Layer

The heat-sensitive recording layer contains a coupler and a diazonium salt compound, and if necessary, may contain other components.

Coupler

The coupler contained in the heat-sensitive recording layer uses at least one type of the pyrrolo[1,2-a]pyrimidine compound selected from the pyrrolo[1,2-a]pyrimidine compound represented by the general formula (1), the pyrrolo[1,2-a]pyrimidine compound represented by the general formula (2) and the pyrrolo[1,2-a]pyrimidine compound represented by the general formula (3). A single pyrrolo[1,2-a]pyrimidine compound or two or more types of the above compounds may be used.

The coupler described above participates in a coupling reaction with a diazo compound in a basic atmosphere and/or neutral atmosphere to form a dye. The coupler in the present invention can be used together with known couplers, in accordance with various objects such as hue control and the like.

Examples of the known couplers include a so-called active meth,Ilne compound having a methylene group adjacent to a carbonyl group, a phenol derivative, a naphthol derivative and the like. Specific examples thereof preferably include the following compounds, which are used in a range corresponding to the objects of the present invention. Preferable examples include resorcin, phloroglucin, 2,3-dihydroxynaphthalene, sodium 2,3-dihydroxynaphthalene-6-sulfonate, 1-hydroxy-2-naphthoic morpholinopropylamide, sodium 2-hydroxy-3-naphthalenesulfonate, 2-hydroxy-3-naphthalenesulfonic anilide, 2-hydroxy-3-naphthalenesulfonic morpholinopropylamide, 2-hydroxy-3-naphthalenesulfonic-2-ethylhexyloxypropylamide, 2-hydroxy-3-naphthalenesulfonic-2-ethylhexylamide, 5-acetamide-1-naphthol, sodium 1-hydroxy-8-acetamidenaphthalene-3,6-disulfonate, 1-hydroxy-8-acetamidenaphthalene-3,6-disulfonic dianilide, 1,5-dihydroxynaphthalene, 2-hydroxy-3-naphthoic morpholinopropylamide, 2-hydroxy-3-naphthoic octylamide, 2-hydroxy-3-naphthoic anilide, 5,5-dimethyl-1,3-cyclohexanedione, 1,3-cyclopentanedione, 5-(2-n-tetradecyloxyphenyl)-1,3-cyclohexanedione, 5-phenyl-4-methoxycarbonyl-1,3-cyclohexanedione, 5-(2,5-di-n-octyloxyphenyl)-1,3-cyclohexanedione, N,N'-dicyclohexylbarbituric acid, N,N'-di-n-dodecylbarbituric acid, N-n-octyl-N'-n-octadecylbarbituric acid, N-phenyl-N'-(2,5-di-n-oct3, loxyphenyl)barbituric acid, N,N'-bis (octadecyloxycarbonylmethyl)barbituric acid, 1-phenyl-3-methyl-5-pyrazolone, 1-(2,4,6-trichlorophenyl)-3-anilino-5-pyrazolone, 1-(2,4,6-trichlorophenyl)-3-benzamide-5-pyrazolone, 6-hydroxy-4-methyl-3-cyano-1-(2-ethylhexyl)-2-pyridone, 2,4-bis-(benzoylacetamide)toluene, 1,3-bis-(pivaloylacetamidemethyl)benzene, benzoylacetonitrile, thenoylacetonitrile, acetacetanilide, benzoylacetanilide, pivaloylacetanilide, 2-chloro-5-(N-n-butylsulfamoyl)-1-pivaloylacctamidebeizeie, 1-(2-ethylhexyloxypropyl)-3-cyaho- 4-methyl-6-hydlroxy-1,2-dihydropyridine-2-one, 1-(dodecyloxypropyl)-3-acetyl-4-methyl-6-hydroxy-1,2-dihydropyridine-2-one, 1-(4-n-octyloxyphenyl)-3-tert-butyl-5-aminopyrazole and the like.

Details of the couplers are described in Japanese Patent Application Laid-Open (JP-A) Nos. 4-201483, 7-223367, 7-223368, 7-323660, Japanese Patent Application Nos. 5-278608, 5-297024, 6-18669, 6-18670, 7-316280, 8-027095, 8-027096, 8-030799, 8-12610, 8-132394, 8-358755, 8-358756, 9-069990 and the like.

The amount of the coupler added in the heat-sensitive recording layer is approximately from 0.02 through 5 g/m² of the heat-sensitive recording layer, and preferably from 0.1 through 4 g/m² in view of the effects.

An amount added of less than 0.02 g/m² is not preferable from the standpoint of the color forming property, and an amount added of over 5 g/m² is not preferable from the standpoint of suitability for coating.

A water-soluble polymer may be added to the coupler used in the present invention together with other components after which the result is dispersed in a solid state by a sand mill or the like and used. Further, the coupler may be used, together with a suitable emulsification assistant, as an emulsifier.

The solid state dispersing method and emulsifying method are not particularly limited, and conventionally known methods can be used. Details of the above methods are described in Japanese Patent Application Laid-Open (JP-A) Nos. 59-190886, 2-141279 and 7-17145.

Diazonium Salt Compound

The diazonium salt compound used in the present invention is a compound represernted by the following general formula:

(wherein, in the formula, Ar represents an aromatic moiety, and X⁻ represents an acid anion). Further, the diazonium salt compound is a compound that undergoes a coupling reaction with the coupler with heating so as to form color, and is decomposed by light. The maximum absorption wavelength thereof can be controlled by the position and type of the substituent on the Ar moiety.

Specific examples of the diazonium forming a salt include 4-(p-tolylthio)-2,5-dibutoxybenzenediazonium, 4-(4-chlorophenylthio)-2,5-dibutoxybenzenediazonium, 4-(N,N-dimethylamino) benzenediazonium, 4-(N,N-diethylamino) benzenediazonium, 4-(N,N-dipropylamino) benzenediazonium, 4-(N-methyl-N-benzylamino) benzenediazonium, 4-(N,N-dibenzylamino) benzenediazonium, 4-(N-ethyl-N-hydroxyethylamino) benzenediazonium, 4-(N,N-diethylamino)-3-methoxybenzenediazonium, 4-(N,N-dimethylamino)-2-methoxybenzenediazonium, 4-(N-benzoylamino)-2,5-diethoxybenzenediazonium, 4-morpholino-2,5-dibutoxybenzenediazonium, 4-anilinobenzenediazonium, 4-[N-(4-methoxybenzoyl)amino]-2,5-diethoxybenzenediazonium, 4-pyrrolidino-3-ethylbenzenediazonium, 4-[N-(1-methyl-2-(4-methoxyphenoxy)ethyl)-N-hexylamino]-2-hexyloxybenzenediazonium, 4-[N-(2-(4-methoxyphenoxy) ethyl)-N-hexylamino]-2-hexyloxybenzenediazonium, 2-(1-ethylpropyloxy)-4-[di-(di-n-butylaminocarbonylmethyl) amino]benzenediazonium, 2-benzylsulfonyl-4-[N-methyl-N-(2-octanoyloxyethyl)]aminobenzenediazonium and the like.

The maximum absor ption wavelength $\lambda_{max}$ of the diazonium salt compound used in the present invention is preferably 450 nm or less from the standpoint of effects, and further preferably from 290 through 440 nm. Diazonium salt compounds having a $\lambda_{max}$ higher than the above wavelength range are not preferable from the standpoint of storability before processing. Diazonium salt compounds having a $\lambda_{max}$ lower than the above wavelength range are not preferable from the standpoint of image fixing, property, image storability, and hue of the formed cyan color when the diazonium salt compound is used in combination with a coupler.

The diazonium salt compound used in the present invention preferably has 12 or more carbon atoms, solubility in water of 1% or less, and solubility in ethyl acetate of 5% or more.

Among the above diazonium salt compounds, it is further preferable to use diazonium salt compounds represented by the general formulae (4) through (6) from the standpoint of hues of the dyes, image storability and image fixing property.

In the general formula (4), Ar represent s a substituted or unsubstituted aryl group.

Examples of the substituent thereof include an alkyl group, alkoxy group, alklithio group, aryl group, arylox group, arylthio group, acyl group, alkoxecarbonyl group, carbamoyl group, carboamide group, sulfonli broup, sulfamoyl group, sulfonamide group, ureide group, halogen group, amino group, heterocyclic group and the like. The substituents described above may further be substituted.

As the aryl group represented by the Ar, an aryl group hivin 6 throumh 30 carbon atoms is preferable, and examples thereof include, but are not particularly limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Likewise, the above groups may further be substituted by an alkyloxy group, alkylthio group, substituted phenyl group, cyano group, substituted amino group, halogen atom, heterocyclic group or the like.

$R^{11}$ and $R^{12}$ each independently represents a substituted or unsubstituted alkyl group, or a substituted or unsubstituted aryl group. $R^{11}$ and $R^{12}$ may be the same or different from each other.

Examples of the substituent thereof include, but are not limited to, an alkoxy group, alkoxycarbonyl group, alkylsulfonyl group, substituted amino group, substituted amide group, aryl group, aryloxy group and the like.

When $R^{11}$ and $R^{12}$ each independently represents an alkyl group, an alkyl group having 1 through 18 carbon atoms is preferable as the alkyl group, and examples thereof include a methyl group, trifluoromethyl group, ethyl group, propyl group, isopropyl group, butyl group, sec-butyl group, t-butyl group, pentyl group, isopentyl group, cyropentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonyapropyl group, 1-(2',4'-di-t-amylphenyloxy)propyl group, acetylaminoethyl group, 2-(N,N-dimethylamino)ethyl group, 2-(N,N-diethylamino)propyl group, methanesulfonylaminopropyl group, acetylaminoethyl group , 2-(N,N-dimethylamino)ethyl group, 2-(N,N-diethylamino)propyl group and the like.

When $R^{11}$ and $R^{12}$ each independently represents an aryl group, an aryl group having 6 through 30 carbon atoms is preferable as the aryl group, and examples thereof include, but are not particularly limited to, a phenyl group, 2-methylphenyl roup, 2-chlirophenyl group, 2-methoxyphenyl group, 2-butoxyphenyl group, 2-(2-ethylhexyloxy)phenyl group, 2-octoxyphenyl group, 3-(2,4-di-t-pentylphenoxyethoxy)phenyl group, 4-chlorophenyl group, 2, '-dichlorophenyl group, 2,4,6-trimethylamienol group, 3-chlorophenyl group, 3-methylphenyl group, 3-methoxyphenyl group, 3-butoxuphenyl group, 3-cyanophenyl group, 3-(2-ethylhexylox,)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Likewise, the above groups may further be substituted by an alkyloxy group, alkylthio group, substituted phenyl group, cyano group, substituted amino group, halogen atom, heterocyclic group or the like.

In the general formula (5), $R^{14}$, $R^{15}$ and $R^{16}$ each independently represents a substituted or unsubstituted alkyl group, or a substituted or unsubstituted aryl group. $R^{14}$, $R^{15}$ and $R^{16}$ may be the same or different from each other.

Examples of the substituent thereof include an alkyl group, alkoxy group, alkylthio group, aryl group, aryloxy group, arylthio group, acyl group, alkoxycarbonyl group, carbamoyl group, carboamide group, sulfonyl group, sulfamoyl group, sulfonamide group, ureide group, halogen atom, amino group, heterocyclic group and the like.

When $R^{14}$, $R^{15}$ and $R^{16}$ each independently represents an alkyl group, an alkyl group having 1 through 18 carbon atoms is preferable as the alkyl group, and examples thereof include a methyl group, trifluoromethyl group, ethyl group, propyl group, isopropyl group, butyl group, sec-butyl group, t-butyl group, pentyl group, isopentyl group, cyclopentyl group, hexed group, cyclohexyl group, octal group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy)propyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group, 1-methyl-2-(4-methoxyphenoxy)ethyl group, di-n-butylaminocarbonylmethyl group, di-n-octylaminocarbonylmethyl group and the like.

When $R^{14}$, $R^{15}$ and $R^{16}$ each independently represents an aryl group, an aryl group having 6 through 30 carbon atoms is preferable as the aryl group, and examples thereof include, but are not particularly limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2, 4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy) phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Likewise, the above groups may further be substituted by an alkyloxy group, alkylthio group, substituted phenyl group, cyano group, substituted amino group, halogen atom, heterocyclic group or the like.

In the general formula (7), Y represents a hydrogen atom or an —$OR^{13}$ group. In the —$OR^{13}$ group, $R^{13}$ represents a substituted or unsubstituted alkyl group, or a substituted or unsubstituted aryl group.

Examples of the substituent thereof include an alkyl group, alkoxy group, alkylthio group, aryl group, aryloxy group, arylthio group, acyl group, alkoxycarbonyl group, carbamoyl group, carboamide group, sulfonyl group, sulfamoyl group, sulfonamide group, ureide group, halogen atom, amino group, heterocyclic group and the like. From the standpoint of control of hue, Y preferably represents a hydrogen atom or an alkoxy group in which $R^{13}$ is an alkyl group.

When $R^{13}$ in the —$OR^{13}$ group represents an alkyl group, an alkyl group having 1 through 18 carbon atoms is preferable as the alkyl group, and examples thereof include a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy)propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group and the like.

When $R^{13}$ in the —$OR^{13}$ group represents an aryl group, an aryl group having 6 through 30 carbon atoms is preferable as the aryl group, and examples thereof include, but are not particularly limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentyrlphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophlenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Likewise, the above groups may further be substituted by an alkyloxy group, alkylthio group, substituted phenyl group, cyano group, substituted amino group, halogen atom, heterocyclic group or the like.

In the general formula (6), $R^{17}$ and $R^{18}$ each independently represents a substituted or unsubstituted alkyl group, or a substituted or unsubstituted aryl group. $R^{17}$ and $R^{18}$ may be the same or different from each other.

Examples of the substituent thereof include an alkyl group, alkoxy group, alkylthio group, aryl group, aryloxy group, arylthio group, acyl group, alkoxycarbonyl group, carbamoyl group, carboamide group, sulfonyl group, sulfamoyl group, sulfonamide group, ureide group, halogen group, amino group, heterocyclic group and the like.

When $R^{17}$ and $R^{18}$ each independently represents an alkyl group, an alkyl group having 1 through 18 carbon atoms is preferable as the alkyl group, and examples thereof include, but are not particularly limited to, a methyl group, trifluoromethyl group, ethyl group, propyl group, isopropyl group, butrl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenznyl group, triphenylmethyl group, ethoxycarbonylmethyl group, butoxycarbonylmethyl group, 2-ethylhexxyloxycarbonylmethyl group, 2',4'-diisopentylphenyloxymethyl group, 2',4'-di-t-butylphenyloxymethyl group, dibenizlaminocarbonylmethyl group, 2,4-di-t-amylphenyloxypropyl group, ethox,carbonylpropyl group, 1-(2',4'-di-t-amylphenyloxy)propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group and the like.

When $R^{17}$ and $R^{18}$ each independently represents an aryl group, an aryl group having 6 through 30 carbon atoms is preferable as the aryl group, and examples thereof include a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Likewise, the above groups may further be substituted by an alkyloxy group, alkylthio group, substituted phenyl group, cyano group, substituted amino group, halogen atom, heterocyclic group or the like.

In the general formulae (4) through (6), $X^-$ represents an acid anion, and examples of the acid anion include polyfluoroalkylcarboxylic acids having 1 through 9 carbon atoms, polyfluoalkylsulfonic acids having 1 through 9 carbon atoms, boron tetrafluoride, tetraphenylboron, hexafluorophosphoric acid, aromatic carboxylic acids, aromatic sulfonic acids and the like. Hexafluorophosphoric acid is preferable in view of crystallinity.

Examples of the diazonium salt compounds represented by the general formulae (4) through (6) include, but are not limited to, the following compounds.

(4)-1
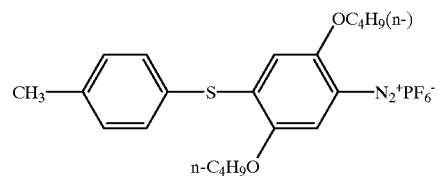

(4)-2
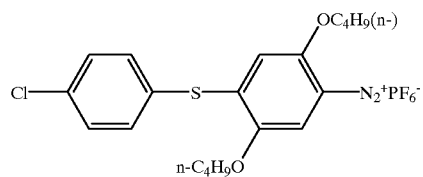

(4)-3
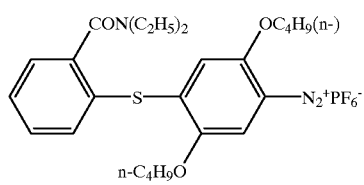

(4)-4
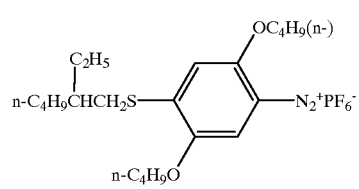

(5)-1
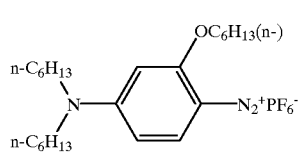

(5)-2
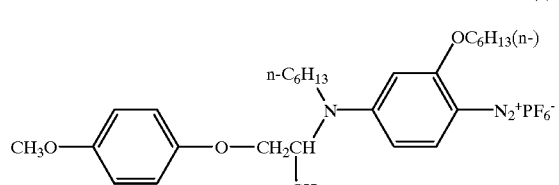

(5)-3
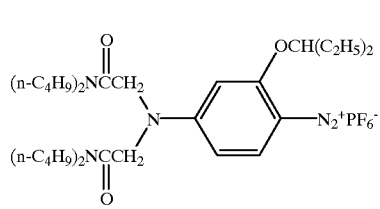

(5)-4
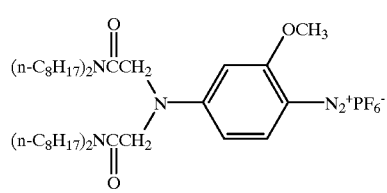

(5)-5
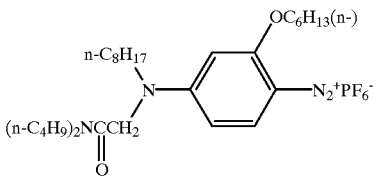

(5)-6
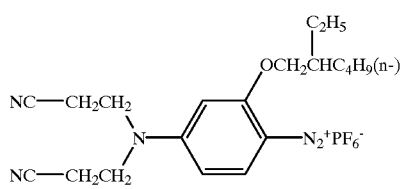

(5)-7
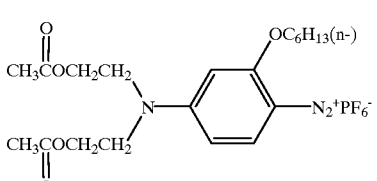

(5)-8
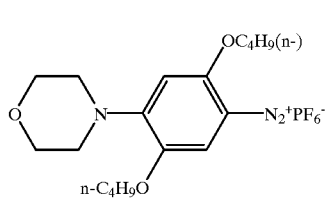

(5)-9
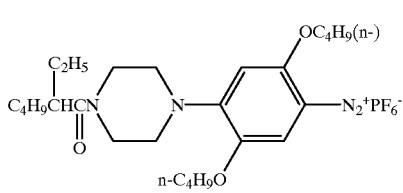

(5)-10
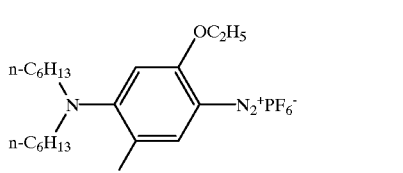

(5)-11
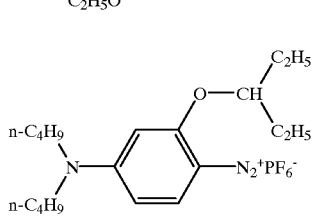

(6)-1
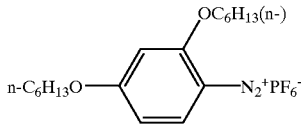

In the present invention, the diazonium salt compounds represented by the general formulae (4) through (6) may be used alone, or two or more types may be used in combination. Further, the diazonium salt compounds represented by the general formulae (4) through (6) may also be used together with known diazonium salt compounds in accordance with various objects such as hue control and the like.

The diazonium salt compound used in the present invention in the heat-sensitive recording layer is preferably contained in an amount of from 0.02 through 3 g/m², and more preferably from 0.1 through 2 g/m².

The diazonium salt compound used in the present invention is preferably encapsulated in microcapsules from the standpoint of storability. The method for preparing the microcapsules is not particularly limited, and the microcapsules can be prepared by a conventionally known method using a wall material such as gelatin, polyurea, polyurethane, polyimide, polyester, polycarbonate, melamine or the like. Of these wall materials, polyurethane and polyurea are preferable from the standpoint of color forming property and storability. Details of methods for preparing the microcapsules are described in Japanese Patent Application Laid-Open (JP-A) No. 2-141279 and the like.

Further, when preparing the microcapsules, an organic solvent having a high boiling point may be used as a dispersion solvent of the diazonium salt compound. The organic solvent is not particularly limited, and conventionally known solvents such as alkyl phthalate, phosphoric ester, citrate, benzoate, alkylamide, fatty ester, trimesilate and the like can be used. Details thereof are described in Japanese Patent Application Laid-Open (JP-A) No. 7-17145 and the like.

Other Components

In the present invention, it is preferable to use organic bases such as tertiary amines, piperidines, piperazines, amidines, formamidines, pyridines, guanidines, morpholines and the like for the purpose of accelerating the coupling reaction.

Specific examples of the organic bases include piperazines such as N,N'-bis(3-phenoxy-2-hydroxypropyl) piperazine, N,N'-bis[3-(p-methylphenoxy)-2-hydroxypropyl]piperazine, N,N'-bis[3-(p-methoxyphenoxy)-2-hydroxypropyl]piperazine, N,N'-bis(3-phenylthio-2-hydroxypropyl)piperazine, N,N'-bis[3-(β-naphthoxy)-2-hydroxypropyl]piperazine, N-3-(β-naphthoxy)-2-hydroxypropyl-N'-methylpiperazine, 1,4-bis{[3-(N-methylpiperadino)-2-hydroxy]propyloxy}benzene and the like, morpholines such as N-[3-(β-naphthoxy)-2-hydroxy]propylmorpholine, 1,4-bis[(3-morpholino-2-hydroxy)propyloxy]benzene, 1,3-bis[(3-morpholino-2-hydroxy)propyloxy]benzene and the like, piperidines such as N-(3-phenoxy-2-hydroxypropyl)piperidine, N-dodecylpiperidine and the like, triphenylguanidine, tricyclohexylguanidine, dicyclohexylphenylguanidine, 2-N-methyl-N-benzylaminoethyl 4-hydroxybenzoate, 2-N,N'-di-n-butylaminoethyl 4-hydroxybenzoate, 4-(3-N,N'-dibutylaminopropoxy)benzenesulfonamide, 4-(2-N,N'-dibutylaminoethoxycarbonyl)phenoxy acetic amide and the like.

Details thereof are described in Japanese Patent Application Laid-Open (JP-A) Nos. 57-123086, 60-49991 and 60-94381, Japanese Patent Application Nos. 7-228731, 7-235157 and 7-235158, and the like. The organic bases described above may be used alone, or two or more types may, be used in combination. The amount of the organic base to be used in the present invention is not particularly limited, but preferably is in a range from 1 through 30 mol per one mol of the diazonium salt compound.

In the present invention, a color forming assistant can also be added in addition to the pyrrolo[1,2-a]pyrimidine compound represented either by the general formula (1), (2) or (3), for the purpose of accelerating the color forming reaction.

Examples of the color forming assistant include phenol derivatives, naphthol derivatives, alkoxy-substituted benzenes, alkoxy-substituted naphthalenes, hydroxy compounds, carboxylic amide compounds, sulfonamide compounds and the like. It is believed that the above compounds lower the melting point of the coupler or the basic substance, or improve the heat permeability of the microcapsule walls, resulting in high density of the formed color.

Method of Preparing a Heat-sensitive Recording Layer

The heat-sensitive recording layer of the present invention can be formed by preparing a coating solution that contains at least one type of the pyrrolo[1,2-a]pyrimidine compound selected from the pyrrolo[1,2-a]pyrimidine compounds represented by the general formula (1), (2) and (3), the diazonium salt compound and other additives, which is then coated on the substrate such as paper, synthetic film or the like by a coating method such as bar coating, blade coating, air knife coating, gravure coating, roll coating, spray coating, dip coating, curtain coating or the like, and is dried. A solid content of the heat-sensitive recording layer is approximately from 2 through 30 g/m².

The binder used in the present invention is not particularly limited, and conventionally knowan binders can be used such as polyvinyl alcohol, hydroxethylcellulose, methylcellulose, carboxymethylcellulose, gelatin, styrene-acrylic acid copolymer and the like. Details thereof are described in Japanese Patent Application Laid-Open (JP-A) No. 2-141279 and the like. In addition, various organic or inorganic pigments, various stabilizers, antioxidants and the like can also be added if necessary.

In the heat-sensitive recording material of the present invention, as described in the above method, at least one type of the pyrrolo[1,2-a]pyrimidine compound selected from the pyrrolo[1,2-a]pyrimidine compounds represented by the general formulae (1), (2) and (3), the diazonium salt compound and the like may be contained in the same layer, or may be contained in separate layers that are layered one upon the other.

Substrate

Conventionally known substrates can be used for the substrate used in the present invention. Specific examples thereof include neutral paper, acidic paper, recycled paper, polyolefine resin-laminated paper, synthetic paper, polyester film, cellulose derivative films such as triacetic cellulose film and the like, polyolefin films such as polystyrene film, polypropylene film, polyethylene film and the like, and they can be used alone, or two or more types can be laminated together for use.

The thickness of the substrate is approximately from 20 through 200 μm. Further, there can also be provided an intermediate layer between the substrate and the heat-sensitive recording layer. Description thereof can be found in Japanese Patent Application Laid-Open (JP-A) No. 61-54980 and the like.

Other Layers and the Like

In the heat-sensitive recording layer of the present invention, a protective layer is preferably provided on the heat sensitive-recording layer, and the protective layer is preferably laminated. The protective layer is formed from a water-soluble polymer, a pigment and the like. To achieve both light resistance and light stability in the protective layer, a compound having a function of controlling ultraviolet ray transmittance is preferably contained in the protective layer. Details of a heat-sensitive recording material containing the compound having a function of controlling ultraviolet ray transmittance are described in Japanese Patent Application Laid-Open (JP-A) No. 7-276808.

The heat-sensitive recording material of the present invention is not limited to the single color but includes a multi-color heat-sensitive recording material as well. Details of the multi-color heat-sensitive recording material are described in Japanese Patent Application Laid-Open (JP-A) Nos. 4-135787, 4-144784, 4-144785, 4-194842, 4-247447, 4-247448, 4-340540, 4-340541, 5-34860 and the like.

Specifically, the multi-color heat-sensitive recording material can be obtained by laminating heat-sensitive recording layers that form colors in different hues. The layer structure is not particularly limited, but one example thereof is a multi-color heat-sensitive recording material prepared by laminating two heat-sensitive recording layers (B layer, C layer), each of the layers obtained by combining a diazonium salt compound having a light-sensitive wavelength that differs from that of the other layer with a coupler that with heating reacts with the diazonium salt compound to form color of a hue that differs from that of the other layer, and a heat-sensitive recording layer (A layer) obtained by combining an electron donating colorless dye with an electron receiving compound.

Specifically, the material comprises a substrate on which are provided a first heat-sensitive recording layer (the A layer) containing the electron donating colorless dye and the electron receiving compound, a second heat-sensitive recording layer (the B layer) containing the diazonium salt compound having a maximum absorption wavelength of 360 nm±20 nm and the coupler that forms color by reacting with the diazonium salt compound during heating, and a third heat-sensitive recording layer (the C layer) containing a diazonium salt compound having a maximum absorption wavelength of 400 nm±20 nm and the coupler that forms color by reacting with the diazonium salt compound during heating. In the above example, if formed color hues in the respective heat-sensitive recording layers are selected such that the three primary colors in subtractive color mixing, i.e., yellow, magenta and cyan, are obtained, full color image recording is made possible.

To record by using the above-described multi-color heat-sensitive recording material, first, the third heat-sensitive recording layer (the C layer) is heated to allow the diazonium salt and the coupler contained in the layer to form color. Then, the unreacted diazonium salt compound contained in the C layer is decomposed and fixed by irradiation of light having a wavelength of 400±20 nm. Thereafter, heat sufficient for color formation of the second heat-sensitive recording layer (the B layer) is applied to allow the diazonium salt compound and the coupler contained in the layer to form color. At this time, although the C layer is simultaneously heated significantly, it does not form color since the diazonium salt compound has already been decomposed (has been fixed bar light) and the color forming ability is lost. Further, the diazonium salt compound contained in the B layer is decomposed by irradiation of light having a wyavelength of 360±20 nm. Lastly, heat sufficient for color formation of the first heat-sensitive recording layer (the A layer) is applied to form color. At this time, although the C and B heat-sensitive recording layers are also heated significantly, they do not form color since the diazonium salt compounds have already been decomposed and their color forming abilities are lost.

Further, all of the heat-sensitive recording layers (the A layer, the B layer and the C layer, in this order from the upper layer) can be heat-sensitive recording layers that are obtained by combining three kinds of diazonium salt compounds having different light-sensitive wavelengths, with couplers that form colors in different hues by reacting with the respective diazonium salt compounds during heating. In particular, by setting the yellow layer having a low luminosity factor as the lowermost layer, effects on images due to roughness on the surface of the substrate can be reduced so as to improve image quality. When all of the heat-sensitive recording layers (the A layer, the B layer and the C layer) are diazo-based heat-sensitive recording layers, it is necessary to carry out light-fixing of the A layer and the B layer after color formation. There is no need to carry out light-fixing for the C layer.

Various fluorescent lamps, xenon lamps, mercury lamps and the like can be used as the light source for fixing used in the above-described fixing by light. It is preferable that the emission spectrum thereof approximately coincides with the absorption spectrum of the diazonium salt compound used in the heat-sensitive material since then efficient light-fixing is made possible.

Further, when recording on the heat-sensitive recording material of the present invention, the heat-sensitive recording material can also be used as a light-sensitive material of a thermal developing type, by which an image can be obtained by exposing the material through an original, decomposing the diazonium salt compounds at portions other than the image formed portions to form a latent image, and thereafter, heating the entire material.

EXAMPLES

Referring now to the following Examples, the present invention will be described further in detail, but the scope thereof will not be limited by the following Examples.

It should be noted that in Examples, all "parts" are "parts by weight". The numbers in parentheses after "coupler" are the numbers in parentheses in Tables 1 though 7 in which specific examples of couplers are listed.

Pyrrolo[1,2-a]pyrimidine Compound Represented by the General Formula (1) or (2)

Example 1

Synthesis of 2-(4-chlorophenyl)-3-(2,6-di-t-butyl-4-methyl) cyclohexyloxycarbonyl-5-amino-6-acetyl-pyrrolo[1,2-a] pyrimidine (coupler (6)):

10 g (19.5 mmol) of 2-(4-chlorophenyl)-3-(2,6-di-t-butyl-4-methyl)cyclohexyloxycarbonyl-5-amino-pyrrolo[1,2-a] pyrimidine was dissolved in 60 ml of tetrahydrofuran (heated to 50° C.). To this was added dropwise 7.7 g (97.7 mmol) of acetylchloride at 50° C. Then, the solution was stirred for 7 hours while being refluxed. After it was cooled, water was added to the resulting reaction solutioin. Then, the reaction product was extracted with ethyl acetate, washed and dried. After the solvent was distilled off, methanol was added to the residue, and the precipitated solid was filtered out. Further, the filtered solid was washed first by methanol and then by hexane, to obtain 6.5 g of 2-(4-chlorophenyl)-3-(2,6-di-t-butyl-4-methyl)cyclohexyloxycarbonyl-5-amino-6-acetyl- pyrrolo[1,2-a]pyrimidine in the form of a white solid (yield: 58%).

The melting point was 195° C. The results of the analysis are given below.

$^1$H-NMR(CDCl$_3$); δ: 12.6 (s, 1H); 11.20(s, 1H); 9.50 (brs, 1H); 7.36 (d, 2H); 7.27 (d, 2H); 5.80 (s, 1H); 2.73 (s, 3H); 1.10 through 1.35 (m); 0.95 through 1.05 (m); 0.77 (s, 21H); 0.42 through 0.58 (m).

Example 2
Synthesis of 2-(4-chlorophenyl)-3-(2,6-di-t-butyl-4-methyl) cyclohexyloxycarbonyl-5-amino-6-phenoxyacetyl-pyrrolo [1,2-a]pyrimidine (coupler (7)):

10 g (19.5 mmol) of 2-(4-chlorophenyl)-3-(2,6-di-t-butyl-4-methyl)cyclohexyloxycarbonyl-5-amino-pyrrolo[1,2-a] pyrimidine was dissolved in 60 ml of tetrahydrofuran (heated to 50° C.). To this was added dropwise 16.6 g (97.7 mmol) of phenoxyacetylchloride at 50° C. Then, the solution was stirred for 2 hours while being refluxed. After it was cooled, water was added to the resulting reaction solution. Then, the reaction product was extracted with ethyl acetate, washed and dried. Thereafter, the solvent was distilled off. The residue was recrystalized by ethyl acetate/methanol, to obtain 9.4 g of 2-(4-chlorophenyl)-3-(2,6-di-t-butyl-4-methyl)cyclohexyloxycarbonyl-5-amino-6-phenoxyacetyl-pyrrolo[1,2-a]pyrimidine in the form of a white solid (yield: 74%).

The melting point was 192° C. The results of the analysis are given below.

$^1$H-NMR (CDCl$_3$); δ: 12.60 (s, 1H); 11.20 (s, 1H); 9.50 (brs, 1H); 7.37 (d, 2H); 7.23 through 7.30 (m, 4H); 6.91 through 6.98 (m, 3H); 5.81 (s, 1H); 5.46 (s, 2H); 1.10 through 1.35 (m); 0.95 through 1.05 (m); 0.76 (s, 2H); 0.42 through 0.58 (m).

Example 3
Synthesis of 2-(3,4-dichlorophenyl)-3-(2,6-di-t-butyl-4-methyl)cyclohexyloxycarbonyl-5-amino-6-(4-methylphenyl)sulfonylcarbamoyl-pyrrolo[1,2-a]pyrimidine (coupler (18)):

1.09 g (2 mmol) of 2-(3,4-dichlorophenyl)-3-(2,6-di-t-butyl-4-methyl)cyclohexyloxycarbonyl-5-amino-pyrrolo[1,2-a]pyrimidine was dissolved in 10 ml of tetrahydrofuran. To this was added dropwise 0.512 g (2.6 mmol) of p-toluenesulfonylisocyanate. Then, the solution was stirred for 30 minutes at room temperature. Water was added to the resulting reaction solution. Then, the reaction product was extracted with ethyl acetate, washed and dried. After being distilled off, the solvent was purified by silica gel column chromatography (hexane/ethyl acetate), to obtain 0.89 g of 2-(3,4-dichlorophenyl)-3-(2,6-di-t-butyl-4-methyl) cyclohexyloxycarbonyl-5-amino-6-(4-methylphenyl) sulfonylcarbamoyl-pyrrolo[1,2-a]pyrimidine in the form of a white solid (yield: 60%).

The melting point was 298° C. (dec.). The results of the analysis are given below.

$^1$H-NMR (CDCl$_3$); δ: 12.58 (s, 1H); 11.20 (s, 1H); 9.47 (brs, 1H); 8.20 (brs, 1H); 7.99 (d, 2H); 7.47 (d, 1H); 7.42 (d, 1H); 7.30 (d, 2H); 7.16 (dd, 1H); 7.05 (s, 1H); 5.85 (s, 1H); 2.42 (s, 3H); 1.20 through 1.40 (m); 1.00 through 1.10 (m); 0.84 (s, 18H); 0.72 (d, 3H); 0.40 through 0.50 (m).

Example 4
Synthesis of 2-(3,4-dichlorophenyl)-3-(2,6-di-t-butyl-4-methyl)cyclohexyloxycarbonyl-5-amino-6-phenylsulfonylcarbamoyl-pyrrolo[1,2-a]pyrimidine (coupler (11)):

The above coupler (11) was obtained in the same manner as in Example 3 except that instead of the p-toluenesulfonylisocyanate used in Example 3, phenylsulfonylisocyanate was used (yield: 63%).

The melting point was 210° C. The results of the analysis are given below.

$^1$H-NMR (CDCl$_3$); δ: 12.60 (s, 1H); 11.20 (s, 1H); 9.45 (brs, 1H); 8.30 (brs, 1H); 8.13 (dd, 2H); 7.50 through 7.65 (m, 3H); 7.49 (d, 1H); 7.41 (d, 1H); 7.17 (dd, 1H); 7.08 (s 1H); 5.87 (s, 1H); 1.20 through 1.40 (m); 1.00 through 1.08 (m); 0.80 (s, 18H); 0.72 (d, 3H); 0.40 through 0.53 (m).

Example 5
Synthesis of 2-(3,4-dichlorophenyl)-3-(2,6-di-t-butyl-4-methyl)cyclohexyloxycarbonyl-5-amino6-(4chlorophenyl) sulfonylcarbamoyl-pyrrolo[1,2a]pyrimidine (coupler (10)):

The above coupler (10) was obtained in the same manner as in Example 3 except that instead of the p-toluenesulfonylisocyanate used in Example 3, p-chlorophenylsulfonylisocyanate was used (yield: 63%)

The melting point was 209° C. The results of the analysis are given below.

$^1$H-NNMR (CDCl$_3$); δ: 12.65 (s, 1H); 11.27 (s, 1H); 9.40 (brs, 1H); 8.35 (brs, 1H); 8.05 (d, 2H); 7.49 (d, 1H); 7.48 (d, 2H); 7.40 (d, 1H); 7.15 (dd, 1H); 7.05 (s, 1H); 5.86 (s, 1H); 1.20 through 1.40 (m); 1.00 through 1.10 (m); 0.84 (s, 18H); 0.71 (d, 3H); 0.40 through 0.53 (m).

Example 6
Synthesis of 2-(3,4-dichlorophenyl)-3-(2,6-di-t-butyl-4-methyl)cyclohexyloxycarbonyl-5- amino-6-ethoxycarbonylcarbamoyl-pyrrolo[1,2-a]pyrimidine (coupler (26)):

The above coupler (26) was obtained in the same manner as in Example 3 except that instead of the p-toluenesulfonylisocyanate used in Example 3, ethoxycarbonylisocyanate was used (yield: 50%).

The melting point was equal to or higher than 300° C. The results of the analysis are given below.

$^1$H-NMR (CDCl$_3$); δ: 12.60 (s, 1H); 10.68 (s, 1H); 10.03 (brs, 1H); 9.31 (brs, 1H); 7.50 (d, 1H); 7.45 (d, 1H); 7.20 (dd, 1H); 7.08(s, 1H); 5.84 (s, 1H); 4.59 (q, 2H); 1.20 through 1.40 (m); 1.00 through 1.10 (mm); 0.86 (s, 18H); 0.75 (d, 3H); 0.40 through 0.54 (m).

Example 7
Synthesis of coupler (49):

5.12 g (10 mmol) of 2-(4-chlorophenyl)-3-(2,6-di-t-butyl-4-methyl)cyclohexyloxycarbonyl-5-amino-pyrrolo[1,2-a] pyrimidine was dissolved in 50 ml of tetrahydrofuran. To this was added dropwise 1.84 g (13 mmol) of chlorosulfonylisocyanate. Then, the solution was stirred for 30 minutes at room temperature. Thereafter, 1.01 g (10 mmol) of triethylamine was added and stirred for another 2 hours at room temperature. Water was added to the resulting reaction solution. Then, the reaction product was extracted with ethyl acetate, washed and dried. After being distilled off, the solvent was purified by silica gel chromatography (hexane/ ethyl acetate), to obtain 2.44 g of the above-described coupler (49) in the form of a white solid (yield: 40%).

The melting point was 202° C. The results of the analysis are given below.

$^1$H-NMR (CDCl$_3$); δ: 11.09 (s, 1H); 10.14 (brs, 1H); 9.35 (brs, 1H); 7.37 (d, 2H); 7.30 (d, 2H); 7.07 (s, 1H); 5.88 (s, 1H); 1.20 through 1.40 (m); 1.00 through 1.10 (m); 0.84 (s, 18H); 0.80 (d, 3H); 0.47 through 0.60 (m).

Heat-sensitive Recording Material

Example 8
Preparation of Microcapsule Liquid A:

To 19 parts of ethyl acetate were added 2.8 parts of a diazonium salt (an example compound (5)-1, maximum absorption wavelength: 370 nm) and 10 parts of tricresyl phosphate, and they were mixed uniformly. Then, to the above mixture was added 7.6 parts of Takenate D-110N (manufactured by Takeda Chemical Industries Ltd.) as a wall agent, and they were mixed uniformly to obtain a liquid I.

Then, to the above liquid I were added 46 parts of an 8% by weight aqueous solution of phthalated gelatin, 17.5 parts of water and 2 parts of a 10% aqueous solution of sodium dodecylbenzenesulfonate, and the mixture was emulsified and dispersed at 10000 r.p.m. for 10 minutes at a temperature of 40° C. To the resultant emulsion was added 20 parts of water and the mixture was made uniform, and thereafter, a microcapsule forming reaction was made to take place for 3 hours at 40° C. while stirring to obtain a microcapsule liquid A. The average particle diameter of the microcapsules was from 0.7 through 0.8 μm.

Preparation of Coupler Emulsified Liquid B:

To 10.5 parts of ethyl acetate were added 3.0 parts of a coupler (6), 3.0 parts of triphenylguanidine, 0.5 parts of tricresyl phosphate and 0.24 parts of diethyl maleate ester to obtain a liquid II.

Then, 49 parts of a 15% by weight aqueous solution of lime-treated gelatin, 9.5 parts of a 10% aqueous solution of sodium dodecylbenzenesulfonate and 35 parts of water were mixed uniformly at 40° C., and to the above mixture was added the liquid II, and the mixture was emulsified and dispersed at 10000 r.p.m. for 10 minutes at a temperature of 40° C. by using a homogenizer. The resultant emulsion was stirred for 2 hours at 40° C. to remove ethyl acetate, and thereafter, water was added in an amount (weight) corresponding to the vaporized ethyl acetate and water, so as to obtain a coupler emulsified liquid B.

Preparation of Heat-sensitive Recording Layer Coating Liquid C:

3.6 parts of the microcapsule liquid A, 3.3 parts of water and 9.5 parts of the coupler emulsified liquid B were uniformly mixed to obtain a heat-sensitive recording layer coating liquid C.

Preparation of Protective Layer Coating Liquid D:

100 parts of a 6% aqueous solution of itaconic acid-modified polvinyl alcohol (trade name: KL-318, manufactured by Kuraray Co., Ltd.) and 10 parts of a 30% dispersion of an epoxy-modified polyamide (trade name: FL-71, manufactured by Toho Chemical Industry Co., Ltd.) were mixed together, and into this wias mixed uniformly 15 parts of a 40% dispersion of zinc stearate (trade name: Hydrin Z, manufactured by Chuko Yusli K.K.) to obtain a protective layer coating liquid D.

Coating:

On a substrate for photographic printing paper which substrate was formed by laminating polyethylene onto a high quality paper, the heat-sensitive recording layer coating liquid C and the protective layer coating liquid D were each coated by using a wire bar and dried at 50° C. in that order to obtain the intended heat-sensitive recording material. The coated amounts in terms of solid components were 8.0 g/m$^2$ and 1.2 g/m$^2$, respectively.

Color Forming Test:

A sample was thermally printed using a thermal head manufactured by Kyocera Corp. (KST type) with the pulse width and power applied to the thermal head having been determined such that the recording energy per unit area was 50 mJ/mm$^2$. Thereafter, the entire surface of the sample was irradiated by light for 15 seconds by using an ultraviolet ray lamp having an emission center wavelength of 365 nm and an output of 40 W. The resultant densities of the image portions and background portions of the sample were measured by a Macbeth densitometer.

Evaluation of Hue:

The reflection spectrum of the image portions, whose color was formed with a thermal head manufactured by Kyocera Corp. (KST type), was measured using a UV/VIS photospectroscope and standarized with the maximum absorbance set at 1.0. A lower absorbance within a wavelength range from 400 through 475 nm means that an excellent cowan color in which there is little yellow has been obtained.

Image Light-resistance Test:

By using a fluorescent lamp light-resistance tester, the image portions, whose color was formed with a thermal head manufactured by Kyocera Corp. (KST type), were irradiated by light continuously for 72 hours at 32,000 lux, and thereafter, the density of the image portions was measured. The higher the density of the image portions after irradiation of light, the more excellent the image light-resistance.

Image Fixing Property Test:

For testing the image fixing property, the background portions (non-printed portions) of the fixed sample were thermally printed by using a thermal head manufactured by Kyocera Corp. (KST type) with the pulse width and power applied to the thermal head having been determined such that the recording energy per unit area was 40 mJ/mm$^2$, and the change in density was measured. The lower the density after printing, the more excellent the image fixing property.

Example 9

A heat-sensitive recording material of Example 9 was prepared and evaluated in the same manner as in Example 8 except that the emulsified liquid was obtained by using a coupler (7) instead of the coupler (6) used in Example 8.

Example 10

A heat-sensitive recording material of Example 10 was prepared and evaluated in the same manner as in Example 8 except that the emulsified liquid was obtained by using a coupler (10) instead of the coupler (6) used in Example 8.

Example 11

A heat-sensitive recording material of Example 11 was prepared and evaluated in the same manner as in Example 8 except that the emulsified liquid was obtained by using a coupler (11) instead of the coupler (6) used in Example 8.

Example 12

A heat-sensitive recording material of Example 12 was prepared and evaluated in the same manner as in Example 8 except that the emulsified liquid was obtained by using a coupler (12) instead of the coupler (6) used in Example 8.

Example 13

A heat-sensitive recording material of Example 13 was prepared and evaluated in the same manner as in Example 8 except that the emulsified liquid was obtained by using a coupler (18) instead of the coupler (6) used in Example 8.

Example 14

A heat-sensitive recording material of Example 14 was prepared and evaluated in the same manner as in Example 8 except that the emulsified liquid was obtained by using a coupler (26) instead of the coupler (6) used in Example 8.

Example 15

A heat-sensitive recording material of Example 15 was prepared and evaluated in the same manner as in Example 8 except that the emulsified liquid asobtained by using a coupler (49) instead of the coupler (6) used in Example 8.

Example 16

A heat-sensitive recording material of Example 16 was prepared and evaluated in the same manner as in Example 13 except that the microcapsule liquid was prepared by using an example compound (4)-2 (maximum absorption wavelength: 370 nm) instead of the diazonium salt (example compound (5)-1) used in Example 13.

Comparative Example 1

A heat-sensitive recording material of Comparative Example 1 was prepared and evaluated in the same manner as in Example 8 except that the emulsified liquid was obtained by using 2-hydroxy-3-naphthoic acid[3-(2-ethylhexyloxy)anilide] instead of the coupler (6) used in Example 8

Values of $\lambda_{max}$ and results of the image light-resistance test and image fixing property test of the image portions are given in Table 17. Data on the absorbance (wavelength range: 400 through 475 nm) of the image portions are given in Table 18.

TABLE 17

| | Color-formed image $\lambda_{max}$ (nm) | Image light-resistance test Density of image portions | | Image fixing property test Density of background portions | | |
|---|---|---|---|---|---|---|
| | | Before irradiation | After irradiation | Before printing | After printing | Hue |
| Example 8 | 658 | 1.57 | 1.33 | 0.07 | 0.12 | cyan |
| Example 9 | 662 | 1.55 | 1.31 | 0.07 | 0.12 | cyan |
| Example 10 | 667 | 1.58 | 1.30 | 0.06 | 0.11 | cyan |
| Example 11 | 666 | 1.50 | 1.32 | 0.06 | 0.10 | cyan |
| Example 12 | 661 | 1.56 | 1.31 | 0.06 | 0.10 | cyan |
| Example 13 | 666 | 1.55 | 1.33 | 0.06 | 0.10 | cyan |
| Example 14 | 660 | 1.54 | 1.34 | 0.07 | 0.12 | cyan |
| Example 15 | 650 | 1.50 | 1.31 | 0.06 | 0.10 | cyan |
| Example 16 | 655 | 1.52 | 1.33 | 0.06 | 0.10 | cyan |
| Comparative Example 1 | 632 | 1.30 | 0.60 | 0.08 | 0.58 | blue |

TABLE 18

| | Absorbance | | |
|---|---|---|---|
| | Wavelength (400 nm) | Wavelength (450 nm) | Wavelength (475 nm) |
| Example 8 | 0.15 | 0.09 | 0.11 |
| Example 9 | 0.16 | 0.09 | 0.10 |
| Example 10 | 0.13 | 0.07 | 0.09 |
| Example 11 | 0.12 | 0.06 | 0.08 |
| Example 12 | 0.13 | 0.07 | 0.08 |
| Example 13 | 0.12 | 0.06 | 0.08 |
| Example 14 | 0.14 | 0.06 | 0.08 |
| Example 15 | 0.13 | 0.08 | 0.09 |
| Example 16 | 0.14 | 0.07 | 0.09 |
| Comparative Example 1 | 0.28 | 0.25 | 0.22 |

From the above results, it can be understood that the heat-sensitive recording material using as the coupler the pyrrolo[1,2-a]pyrimidine compound represented by the general formulae (1) or (2) of the present invention has high density of the formed color. In the image portions, there is little absorption of yellow color, and an excellent cyan color can be obtained. It is further evident that, even after irradiation with a fluorescent lamp, there is little decrease in density of the image portions and the image light-resistance is excellent. Moreover, when the background portions of a sample that has been subjected to image fixing are again thermally, printed, there is little color formation and the image fixingy property is excellent.

Pyrrolo[1,2-a]pyrimidine Compound Represented by the General Formula (3)

It should be noted that in the Examples, all "parts" are "parts by weight". The numbers in parentheses after "coupler" are the numbers in parentheses in Tables 8 though 16 in which specific examples of couplers are listed.

Example 17
Synthesis of Coupler (50):
10 g (19.5 mmol) of 7-(4-chlorophenyl)-8-(2,6-di-t-butyl-4-methyl)cyclohexyloxycarbonyl-2-amino-pyrrolo[1,2-a]pyrimidine-4-on was added to 60 ml of acetonitrile and cooled to 0 through 5° C. To this, 3.6 g (25.4 mmol) of chlorosulfonylisocyanate was added dropwise in such a manner as to keep the reaction temperature below 25° C. Then, the solution was cooled to room temperature and was stirred for 3 hours. Further, the solution was cooled again to 0 through 5° C. To this, 5.15 g (58.5 mmol) of N,N'-dimethylaminoethylamine was added dropwise in such a manner as to keep the reaction temperature below 25° C. Then, the solution was cooled to room temperature and was stirred for 1.5 hours.

Water was added to the resulting reaction solution. Then, the reaction product was extracted with ethyl acetate, washed with a saturated sodium chloride solution and dried. The ethyl acetate was distilled off under reduced pressure. The residue was fractionated by silica gel chrornatography. Methanol was added to the fraction, and the precipitated solid was filtered out to obtain 7.4 g of an example compound (50) in the form of a pale yellow solid (yield: 54%).

m.p. 115.5° C.; $^1$H-NMR (CDCl$_3$) 7.4 (d 2H) 7.25 (d 2H) 5.83 (s 1H) 3.2 (m 2H) 2.55 (m 2H) 0.4 through 1.4 (m 28H).

Example 18
Synthesis of Coupler (58):
15 g (27.4 mmol) of 7-(3,4-dichlorophenyl)-8-(2,6-di-t-butyl-4-methyl)cyclohexyloxycarbonyl-2-amino-pyrrolo[1,2-a]pyrimidine-4-on was added to 80 ml of acetonitrile and cooled to 0 through 5° C. To this, 5 g (35.3 mmol) of chlorosulfonylisocyanate was added dropwise in such a manner as to keep the reaction temperature below 25° C. Then, the solution was cooled to room temperature and was stirred for 3 hours. Further, the solution was cooled again to 0 through 5° C. To this, 8.4 g (82.2 mmol) of trimethylethylenediamine was added dropwise in such a manner as to keep the reaction temperature below 25° C. Then, the solution was cooled to room temperature and was stirred for 1.5 hours.

Water was added to the resulting reaction solution. Then, the reaction product was extracted with ethyl acetate, washed with a saturated sodium chloride solution and dried. The ethyl acetate was distilled off under reduced pressure. The residue was fractionated by silica gel chromatography. Methanol was added to the fraction, and the precipitated solid was filtered out to obtain 10.1 g of an example compound (58) in the form of a white solid (yield: 49%).

m.p. 149.4° C.; $^1$H-NMR (CDCl$_3$) 7.5 (d 2H) 7.1 (d 2H) 7.18 through 7.20 (d-d 1H) 7.05 (s 1H) 5.84 (s 1H) 3.5 (m 2H) 3.0 (s 3H) 2.63 (m 2H) 2.37 (s 6H) 0.4 through 1.4 (m 28H).

Example 19
Synthesis of Coupler (60):
15 g (27.4 mmol) of 7-(3,4-dichlorophenyl)-8-(2,6-di-t-butyl-4-methyl)cyclohexyloxycarbonyl-2-amino-pyrrolo[1, 2-a]pyrimidine-4-on was added to 80 ml of acetonitrile and cooled to 0 through 5° C. To this, 5 g (35.3 mmol) of chlorosulfonylisocyanate was added dropwise in such a manner as to keep the reaction temperature below 25° C. Then, the solution was cooled to room temperature and was stirred for 3 hours. Further, the solution was cooled again to 0 through 5° C. To this, 8.2 g (82.2 mmol) of N-methylpiperazine was added dropwise in such a manner as to keep the reaction temperature below 25° C. Then, the solution was cooled to room temperature and was stirred for 1.5 hours.

Water was added to the resulting reaction solution. Then, the reaction product was extracted with ethyl acetate, washed with a saturated sodium chloride solution and dried. The ethyl acetate was distilled off under reduced pressure. Methanol was added to the residue, and the precipitated solid was filtered out to obtain 14.2 g of example compound (60) in the form of a white solid (yield: 69%).

m.p. 136.3° C.;

$^1$H-NMR (CDCl$_3$) 12.8 (s 1H) 7.5 (d 2H) 7.41 (d 2H) 7.18 through 7.20 (d-d 1H) 7.03 (s 1H) 3.48 (m 2H) 2.58 (m 2H) 2.40 (s 3H) 0.4 through 1.4 (mn 28H).

Example 20

Synthesis of coupler (66):

10 g (19.5 mmol) of 7-(4-chlorophenyl)-8-(2,6-di-t-butyl-4-methyl)cyclohexyloxycarbonyl-2-amino-pyrrolo[1,2-a]pyrimidine-4-on was added to 80 ml of acetonitrile and cooled to 0 through 5° C. To this, 5 g (35.3 mmol) of chlorosulfonylisocyanate was added dropwise in such a manner as to keep the reaction temperature below 25° C. Then, the solution was cooled to room temperature and was stirred for 3 hours. Further, the solution was cooled again to 0 through 5° C. To this, 5.3 g of N-methyl-aniline (49 mmol) was added dropwise in such a manner as to keep the reaction temperature below, 25° C. Then, the solution was cooled to room temperature and was stirred for 1.5 hours.

Water was added to the resulting reaction solution. Then, the reaction product was extracted with ethyl acetate, washed with a saturated sodium chloride solution and dried. The ethyl acetate was distilled off under reduced pressure. Methanol was added to the residue, and the precipitated solid was filtered out to obtain 10.3 g of an example compound (66) in the form of a white solid (yield: 70.7%).

m.p. 171.4° C,;

$^1$H-NMR (CDCl$_3$) 12.22 (s 1H) 10.6 (s 1H) 7.24 through 7.45 (m 9H) 7.02 (s 1H) 5.86 (s 1H) 3.54 (s 3H) 0.4 through 1.4 (m 28H).

Example 21

Synthesis of Coupler (68):

15 g (50.5 mmol) of 7-phenyl-8-ethoxycarbonyl-2-amino-pyrrolo[1,2-a]pyrimidine-4-on was added to 100 ml of acetonitrile and cooled to 0 through 5° C. To this, 8.6 g (60.8 mmol) of chlorosulfonylisocyanate was added dropwise in such a mannier is to keep the reaction temperature below 25° C. Then, the solution was cooled to room temperature and was stirred for 3 hours. Further, the solution was cooled again to 0 through 5° C. To this, 13.5 g (126.2 mmol) of N-methyl-aniline was added dropwise in such a manner as to keep the reaction temperature below 25° C. Then, the solution was cooled to room temperature and was stirred for 1.5 hours.

Water was added to the resulting reaction solution. Then, the reaction product was extracted with ethyl acetate, washed with a saturated sodium chloride solution and dried. The ethyl acetate was distilled off under reduced pressure. The residue was fractionated by silica gel chromatography. Methanol was added to the fraction, and the precipitated solid was filtered to obtain 13.8 g of an example compound (68) in the form of a white solid (yield: 53.7%).

m.p. 134.8° C.;

$^1$H-NMR (CDCl$_3$) 12.42 (s 1H) 10.23 (s 1H) 7.26 through 7.48 (m 1OH) 7.18 (s 1H) 4.23 (q 2H) 3.53 (s 3H) 1.24 (t 3H).

Example 22

Synthesis of Coupler (69):

15 g (50.5 mmol) of 7-phenyl-8-ethoxycarbonyl-2-amino-pyrrolo[1,2-a]pyrimidine-4-on was added to 100 ml of acetonitrile and cooled to 0 through 5° C. To this, 8.6 g (60.8 mmol) of chlorosulfonylisocyanate was added dropwise in such a manner as to keep the reaction temperature below 25° C. Then, the solution was cooled to room temperature and was stirred for 3 hours. Further, the solution was cooled again to 0 through 5° C. To this, 17.0 g (126 mmol) of 3-isopropyl-aniline was added dropwise in such a manner as to keep the reaction temperature below 25° C. Then, the solution was cooled to room temperature and was stirred for 1.5 hours.

Water was added to the resulting reaction solution. Then, the reaction product was extracted with ethyl acetate, washed with a saturated sodium chloride solution and dried. The ethyl acetate was distilled off under reduced pressure. The residue was fractionated by silica gel chromatography. Methanol was added to the fraction, and the precipitated solid was filtered out to obtain 15.1 g of an example compound (69) in the form of a pale yellow solid (yield: 55.7%).

m.p. 220.7° C.;

$^1$H-NMR (CDCl$_3$) 12.5 (s 1H) 10.81 (s 1H) 8.87 (s 1H) 7.06 through 7.5 (m 9H) 7.1 (s 1H) 4.1 (q 2H) 2.84 (m 1H) 1.12 (d 6H) 1.06 (t 3H).

It should be noted that other pyrrolo[1,2-a]pyrimidine compounds can be synthesized in the same manner.

Example 23

Preparation of Heat-sensitive Recording Material:
Preparation of Microcapsule Liquid A:

To 19 parts of ethyl acetate were added 2.8 parts of a diazonium salt (example compound (4)-1, maximum absorption wavelength: 370 nm) and 10 parts of tricresyl phosphate, and they were mixed uniformly. Then, to the above mixture was added 7.6 parts of Takenate D-110N (manufactured by, Takeda Chemical Industries Ltd.) as a wall agent, and they were mixed uniformly to obtain a liquid I.

Then, to the above liquid I were added 46 parts of an 8% by weight aqueous solution of phthalated gelatini, 17.5 parts of water and 2 parts of a 10% aqueous solution of sodium dodecylbenzenesulfonate, and the mixture was emulsified and dispersed at 10000 r.p.m. for 10 minutes at a temperature of 40° C. To the resultant emulsion was added 20 parts of water and the mixture was made uniform, and thereafter, a microcapsule forming reaction was made to take place for 3 hours at 40° C. while stirring to obtain a microcapsule liquid A. The average particle diameter of the microcapsules was from 0.7 through 0.8 µm.

Preparation of Coupler Emulsified Liquid B:

To 10.5 parts of ethyl acetate were added 3.0 parts of a coupler (an example compound (4)), 3.0 parts of triphenylguanidine, 0.5 parts of tricresyl phosphate and 0.24 parts of diethyl maleate to obtain a liquid II.

Then, 49 parts of a 15% by weight aqueous solution of lime-treated gelatin, 9.5 parts of a 10% aqueous solution of sodium dodecylbenzenesulfonate and 35 parts of water were mixed uniformly at 40° C., and to the above mixture was added the liquid II, and the mixture was emulsified and dispersed at 10000 r.p.m. for 10 minutes at a temperature of 40° C. by using a homogenizer. The resultant emulsion was stirred for 2 hours at 40° C. to remove ethyl acetate, and thereafter, water was added in an amount (weight) corresponding to the vaporized ethyl acetate and water, so as to obtain a coupler emulsified liquid B.

Preparation of Heat-sensitive Recording Layer Coating Liquid C:

3.6 parts of the microcapsule liquid A, 3.3 parts of water and 9.5 parts of the coupler emulsified liquid B were uniformly mixed to obtain a heat-sensitive recording layer coating liquid C.

Preparation of Protective Layer Coating Liquid D:

100 parts of a 6% aqueous solution of itaconic acid-modified polyvinyl alcohol (trade name: KL-318, manufactured by, Kuraray Co., Ltd.) and 10 parts of a 30% dispersion of an epoxy-modified polyamide (trade name: FL-71, manufactured by Toho Chemical Industry Co., Ltd.) were mixed together, and into this was mixed uniformly 15 parts of a 40% dispersion of zinc stearate (trade name: Hydrin Z, manufactured by Chukyo Yushi K.K.) to obtain a protective layer coating liquid D.

Coating:

On a substrate for photographic printing paper which substrate was formed by laminating polyethylene onto a high quality paper, the heat-sensitive recording layer coating liquid C and the protective layer coating liquid D were each coated by using a wire bar and dried at 50° C. in that order to obtain the intended heat-sensitive recording material. The coated amounts in terms of solid components were 8.0 g/m$^2$ and 1.2 g/m$^2$, respectively.

Color Forming Test:

A sample was thermally printed using a thermal head manufactured by Kyocera Corp. (KST type) with the pulse width and power applied to the thermal head having been determined such that the recording energy per unit area was 50 mJ/mm$^2$. Thereafter, the entire surface of the sample was irradiated by light for 15 seconds by using an ultraviolet ray lamp having an emission center wavelength of 365 nm and an output of 40 W. The resultant densities of the image portions and background portions of the sample were measured by a Macbeth densitometer.

Image Light-resistance Test:

By using a fluorescent lamp light-resistance tester, the image portions, whose color was formed with a thermal head manufactured by Kvocera Corp. (KST typc), wacre irradiated byd light continuously for 24 hours at 30,000 lux, and thereafter, the density of the image portions was measured. The higher the density of the image portions after irradiation of light, the more excellent the image light-resistance.

Image Fixing Property Test:

For testing the image fixing property, the background portions (non-printed portions) of the fixed sample were thermally printed by using a thermal head manufactured by Kyocera Corp. (KST type) with the pulse width and power applied to the thermal head having been determined such that the recording energy per unit area was 40 mJ/mm$^2$, and the change in density was measured. The lower the density after printing, the more excellent the image fixing property.

Example 24

A heat-sensitive recording material of Example 24 was prepared and evaluated in the same manner as in Example 23 except that the emulsified product was obtained by using a coupler (9) instead of the coupler (4) used in Example 23.

Example 25

A heat-sensitive recording material of Example 25 was prepared and evaluated in the same manner as in Example 23 except that the emulsified product was obtained by using a coupler (16) instead of the coupler (4) used in Example 23.

Example 26

A heat-sensitive recording material of Example 26 was prepared and evaluated in the same manneir as in Example 23 exccpt that the emulsified product was obtained by using a coupler (21) instead of the coupler (4) used in Example 23.

Example 27

A heat-sensitive recording material of Example 27 was prepared and evaluated in the same manner as in Example 23 except that the emulsified product was obtained by using a coupler (27) instead of the coupler (4) used in Example 23.

Example 28

A heat-sensitive recording material of Example 28 was prepared and evaluated in the same manner as in Example 23 except that the emulsified product was obtained by using a coupler (32) instead of the coupler (4) used in Example 23.

Example 29

A heat-sensitive recording material of Example 29 was prepared and evaluated in the same manner as in Example 23 except that the emulsified product was obtained by using a coupler (35) instead of the coupler (4) used in Example 23.

Example 30

A heat-sensitive recording material of Example 30 was prepared and evaluated in the same manner as in Example 23 except that the emulsified product was obtained by using a coupler (40) instead of the coupler (4) used in Example 23.

Example 31

A heat-sensitive recording material of Example 31 was prepared and evaluated in the same manner as in Example 23 except that the emulsified product was obtained by using a coupler (41) instead of the coupler (4) used in Example 23.

Example 32

A heat-sensitive recording material of Example 32 was prepared and evaluated in the same manner as in Example 23 except that the emulsified product was obtained by using a coupler (44) instead of the coupler (4) used in Example 23.

Example 33

A heat-sensitive recording material of Example 33 was prepared and evaluated in the same manner as in Example 23 except that the emulsified product was obtained by using a coupler (46) instead of the coupler (4) used in Example 23.

Example 34

A heat-sensitive recording material of Example 34 was prepared and evaluated in the same manner as in Example 23 except that the emulsified product was obtained by using the coupler (49) instead of the coupler (4) used in Example 23.

Example 35

A heat-sensitive recording material of Example 35 was prepared and evaluated in the same mannier as in Example 23 except that the emulsified product was obtained by using a coupler (50) instead of the coupler (4) used in Example 23.

Example 36

A heat-sensitive recording material of Example 36 was prepared and evaluated in the same manner as in Example 23 except that the emulsified product was obtained by using a coupler (55) instead of the coupler (4) used in Example 23.

Example 37

A heat-sensitive recording material of Example 37 was prepared and evaluated in the same manner as in Example 23 except that the microcapsule liquid was prepared by using an example compound (3)-2 (maximum absorption wavelength: 365 nm) instead of the diazonium salt (the example compound (4)-1) used in Example 23.

Example 38

A heat-sensitive recording material of Example 38 was prepared and evaluated in the same manner as in Example 23 except that the emulsified product was obtained by using a coupler (56) instead of the coupler (4) used in Example 23.

Example 39

A heat-sensitive recording material of Example 39 was prepared and evaluated in the same manner as in Example 23 except that the emulsified product was obtained by using a coupler (58) instead of the coupler (4) used in Example 23.

Example 40

A heat-sensitive recording material of Example 40 was prepared and evaluated in the same manner as in Example 23 except that the emulsified product was obtained by using a coupler (59) instead of the coupler (4) used in Example 23.

Example 41

A heat-sensitive recording material of Example 41 was prepared and evaluated in the same manner as in Example 23 except that the emulsified product was obtained by using a coupler (60) instead of the coupler (4) used in Example 23.

Example 42

A heat-sensitive recording material of Example 42 was prepared and evaluated in the same manner as in Example 23 except that the emulsified product was obtained by using a coupler (61) instead of the coupler (4) used in Example 23.

Example 43

A heat-sensitive recording material of Example 43 was prepared and evaluated in the same manner as in Example 23 except that the emulsified product was obtained by using a coupler (66) instead of the coupler (4) used in Example 23.

Example 44

A heat-sensitive recording material of Example 44 was prepared and evaluated in the same manner as in Example 23 except that the emulsified product was obtained by using a coupler (67) instead of the coupler (4) used in Example 23.

Example 45

A heat-sensitive recording material of Example 45 was prepared and evaluated in the same manner as in Example 23 except that the emulsified product was obtained by using a coupler (68) instead of the coupler (4) used in Example 23.

Example 46

A heat-sensitive recording material of Example 46 was prepared and evaluated in the same manner as in Example 23 except that the emulsified product was obtained by using a coupler (69) instead of the coupler (4) used in Example 23.

Example 47

A heat-sensitive recording material of Example 47 was prepared and evaluated in the same manner as in Example 23 except that the emulsified product was obtained by using a coupler (72) instead of the coupler (4) used in Example 23.

Comparative Example 2

A heat-sensitive recording material of Comparative Example 2 was prepared and evaluated in the same manner as in Example 23 except that the emulsified product was obtained by using 2-hydroxy-3-naplhthoic acid[3-(2-ethylhexyloxy)anilide] instead of the coupler (4) used in Example 23.

Values of $\lambda_{max}$ and results of the image light-resistance test and fixing property test of the image portions are given in Tables 19 and 20.

TABLE 9

| Examples | Color-formed image $\lambda_{max}$ (nm) | Color forming property | Image light-resistance Density after irradiation | Image fixing property test Density of background portions Before printing | After printing |
| --- | --- | --- | --- | --- | --- |
| Example 23 | 685 | 1.78 | 1.55 | 0.06 | 0.08 |
| Example 24 | 695 | 1.79 | 1.54 | 0.07 | 0.09 |
| Example 25 | 684 | 1.80 | 1.61 | 0.06 | 0.09 |
| Example 26 | 697 | 1.77 | 1.54 | 0.07 | 0.09 |
| Example 27 | 690 | 1.70 | 1.50 | 0.07 | 0.10 |
| Example 28 | 702 | 1.72 | 1.51 | 0.08 | 0.10 |
| Example 29 | 665 | 1.78 | 1.52 | 0.07 | 0.09 |
| Example 30 | 674 | 1.77 | 1.50 | 0.09 | 0.11 |
| Example 31 | 661 | 1.80 | 1.62 | 0.07 | 0.10 |
| Example 32 | 660 | 1.81 | 1.61 | 0.08 | 0.10 |
| Example 33 | 658 | 1.70 | 1.51 | 0.07 | 0.09 |
| Example 34 | 670 | 1.72 | 1.51 | 0.08 | 0.11 |
| Example 35 | 671 | 1.68 | 1.48 | 0.09 | 0.12 |

TABLE 20

| Examples, Comparative Examples | Color-formed image $\lambda_{max}$ (nm) | Color forming property | Image light-resistance Density after irradiation | Image fixing property test Density of background portions Before printing | After printing |
| --- | --- | --- | --- | --- | --- |
| Example 36 | 655 | 1.81 | 1.62 | 0.06 | 0.09 |
| Example 37 | 698 | 1.83 | 1.64 | 0.06 | 0.08 |
| Example 38 | 651 | 1.84 | 1.63 | 0.06 | 0.09 |
| Example 39 | 667 | 1.81 | 1.60 | 0.06 | 0.09 |
| Example 40 | 660 | 1.81 | 1.61 | 0.07 | 0.10 |
| Example 41 | 665 | 1.79 | 1.58 | 0.07 | 0.09 |
| Example 42 | 654 | 1.80 | 1.59 | 0.06 | 0.09 |
| Example 43 | 653 | 1.83 | 1.61 | 0.06 | 0.08 |
| Example 44 | 656 | 1.79 | 1.60 | 0.07 | 0.08 |

TABLE 20-continued

| Examples, Comparative Examples | Color-formed image $\lambda_{max}$ (nm) | Color forming property | Image light-resistance Density after irradiation | Image fixing property test Density of background portions | |
|---|---|---|---|---|---|
| | | | | Before printing | After printing |
| Example 45 | 645 | 1.85 | 1.64 | 0.06 | 0.08 |
| Example 46 | 647 | 1.84 | 1.65 | 0.06 | 0.08 |
| Example 47 | 657 | 1.77 | 1.55 | 0.07 | 0.09 |
| Comparative Example 2 | 639 | 1.23 | 0.55 | 0.09 | 0.55 |

From the results described above, it is made evident that a heat-sensitive recording material of a purple-to-cyan color forming type, which uses as a coupler a pyrrolo[1,2-a]pyrimidine compound represented by the general formula (3) has high density of the formed color. It is further evident that, even after irradiation with a fluorescent lamp, there is little decrease in density of the image portions and the image light-resistance is excellent. Moreover, when the background portions of a sample that has been subjected to image fixing are again thermally printed, there is little color formation and the image fixing property is excellent.

According to the present invention, there can be provided a novel pyrrolo[1,2-a]pyrimidine compound that, when coupled with a diazonium salt serving as a coupler, can not only provide excellent color forming property but can also produce a cyan dyethat has low absorption of yellow color. Further, in accordance with the present invention, by combining the above pyrrolo[1,2-a]pyrimidine compound with a diazonium salt compound, there can be provided a novel diazo heat-sensitive recording material of a cyan color forming type having excellent shelf life, image light-resistance and image fixing property in addition to the above-described properties.

What is claimed is:

1. A pyrrolo[1,2-a]pyrimidine compound represented by following general formula (1):

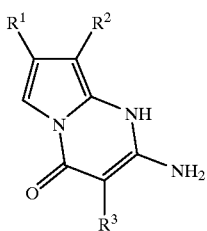

General formula (1)

wherein, in the general formula (1), $R^1$ and $R^2$ each independently represents a hydrogen atom, halogen atom, aryl group, alkyl group, cyano group, acyl group, carbamoyl group, alkoxycarbonyl group, aryloxycarbonyl group, alkl-sulfonyl group or arylsulfonyl group; and $R^3$ represents an electron attractive group whose Hammett's substituent constant $\sigma_p$ value is equal to or larger than 0.20.

2. A pyrrolo[1,2-a]pyrimidine compound represented by following general formula (2):

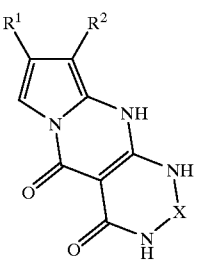

General formula (2)

wherein, in the general formula (2), $R^1$ and $R^2$ each independently represents a hydrogen atom, halogen atom, aryl group, alkyl group, cyano group, acyl group, carbamoyl group, alkoxycarbonyl group, aryloxycarbonyl group, alkl-sulfonyl group or arylsulfonyl group; and X represents CO or $SO_2$.

3. A pyrrolo[1,2-a]pyrimidine compound represented by following general formula (3):

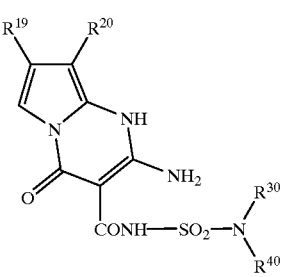

General formula (3)

wherein, in the general formula (3), $R^{19}$ and $R^{20}$ each independently represents a hydrogen atom, halogen atom, aryl group, alkyl group, cyano group, acyl group, substituted carbamoyl group, alkoxycarbonyl group, aryloxycarbonyl group, acyloxy group, alkoxy group, aryloxy group, alkylthio group, arylthio group, substituted sulfamoyl group, alkylsulfonyl group, arylsulfonyl group, alkylphosphoryl group, arylphosphoryl group or substituted amino group; $R^{30}$ and $R^{40}$ each independently represents a hydrogen atom, alkyl group, aryl group, cycloalkyl group, piperidyl group, acyl group, $-C_nH_{2n}N(R^{50})(R^{60})$ or $-C_mH_{2m}XC_lH_{2l}N(R^{70})(R^{80})$; $R^{50}$ through $R^{80}$ each independently represents a hydrogen atom, alkyl group or aryl group; X represents an oxygen atom, sulfur atom or $N(R^{90})-$; $R^{90}$ represents a hydrogen atom, alkyl group or aryl group; $R^{30}$ and $R^{40}$, or $R^{50}$ and $R^{60}$, or $R^{70}$ and $R^{80}$, or $R^{70}$ and $R^{90}$, or $R^{80}$ and $R^{90}$ may combine with each other to form a ring, and in the case of ring formation, they may contain a hetero atom; and n, m and l represent integers from 1 through 12.

4. A method of preparing a pyrrolo[1,2-a]pyrimidine compound, which is a method of preparing the pyrrolo[1,2-a]pyrimidine compound of claim 3, wherein a pyrrolo[1,2-a]pyrimidine compound represented by following formula (A) is first reacted with chlorosulfonylisocyanate ($ClSO_2NCO$), and thereafter, reacted with $HN(R^{30})(R^{40})$:

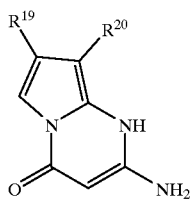

(A)

wherein, $R^{19}$ and $R^{20}$ in the above formula (A) have the same meanings as those of $R^{19}$ and $R^{20}$ in the general formula (3) of claim 3, respectively; and $R^{30}$ and $R^{40}$ in $HN(R^{30})(R^{40})$ have the same meanings as those of $R^{30}$ and $R^{40}$ in the general formula (3) of claim 3, respectively.

5. A heat-sensitive recording material comprising a substrate, and on the substrate, a heat-sensitive recording layer containing a diazonium salt compound and a coupler that forms color by reacting with the diazonium salt compound during heating, wherein the coupler contains at least one type of the pyrrolo[1,2-a]pyrimidine compound represented by the general formula (1) of claim 1, the pyrrolo[1,2-a]pyrimidine compound represented by the general formula (2) of claim 2 or the pyrrolo[1,2-a]primidine compound represented by the general formula (3) of claim 3.

6. A heat-sensitive recording material according to claim 5, wherein maximum absorption wavelength $\lambda_{max}$ of the diazonium salt compound is 450 nm or less.

7. A heat-sensitive recording material according to claim 5, wherein the diazonium salt compound is at least one type of the compounds represented by one of following general formulae (4) through (6):

General formula (4)

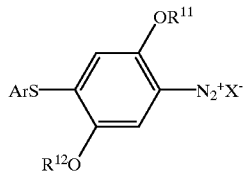

wherein, in the general formula (4), Ar represents a substituted or unsubstituted aryl group; $R^{11}$ and $R^{12}$ each independently represents a substituted or unsubstituted alkyl group, or a substituted or unsubstituted aryl group; $R^{11}$ and $R^{12}$ may be the same or different from each other; and $X^-$ represents an acid anion;

General formula (5)

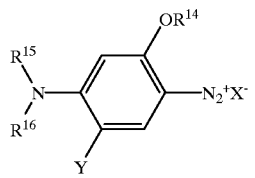

wherein, in the general formula (5), $R^{14}$, $R^{15}$ and $R^{16}$ each independently represents a substituted or unsubstituted alkyl group, or a substituted or unsubstituted aryl group; $R^{14}$, $R^{15}$ and $R^{16}$ may be the same or different from each other; Y represents a hydrogen atom or a $-OR^{13}$ group; $R^{13}$ represents a substituted or unsubstituted alkyl group, or a substituted or unsubstituted aryl group; and $X^-$ represents an acid anion;

General formula (6)

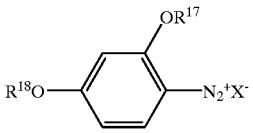

wherein, in the general formula (6), $R^{17}$ and $R^{18}$ each independently represents a substituted or unsubstituted alkyl group, or a substituted or unsubstituted aryl group; and $X^-$ represents an acid anion.

8. A heat-sensitive recording material according to claim 6, wherein the diazonium salt compound is at least one type of the compounds represented by one of following general formulae (4) through (6):

General formula (4)

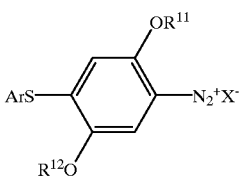

wherein, in the general formula (4), Ar represents a substituted or unsubstituted aryl group; $R^{11}$ and $R^{12}$ each independently represents a substituted or unsubstituted alkyl group, or a substituted or unsubstituted aryl group; $R^{11}$ and $R^{12}$ may be the same or different from each other; and $X^-$ represents an acid anion;

General formula (5)

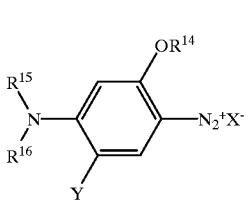

wherein, in the general formula (5), $R^{14}$, $R^{15}$ and $R^{16}$ each independently represents a substituted or unsubstituted alkyl group, or a substituted or unsubstituted aryl group; $R^{14}$, $R^{15}$ and $R^{16}$ may be the same or different from each other; Y represents a hydrogen atom or a $-OR^{13}$ group; $R^{13}$ represents a substituted or unsubstituted alkyl group, or a substituted or unsubstituted aryl group; and $X^-$ represents an acid anion;

General formula (6)

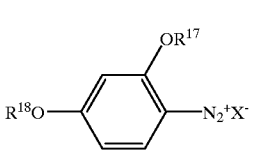

wherein, in the general formula (6), $R^{17}$ and $R^{18}$ each independently represents a substituted or unsubstituted alkyl group, or a substituted or unsubstituted aryl group; and $X^-$ represents an acid anion.

9. A heat-sensitive recording material according to claim 5, wherein the diazonium salt compound is encapsulated in microcapsules.

10. A heat-sensitive recording material according to claim 6, wherein the diazonium salt compound is encapsulated in microcapsules.

11. A heat-sensitive recording material according to claim 7, wherein the diazonium salt compound is encapsulated in microcapsules.

12. A heat-sensitive recording material according to claim 8, wherein the diazonium salt compound is encapsulated in microcapsules.

13. A heat-sensitive recording material according to claim 6, wherein capsule walls of the microcapsules comprise polyurethane and/or polyurea as components.

* * * * *